United States Patent [19]

McCandliss et al.

[11] Patent Number: 5,213,972
[45] Date of Patent: May 25, 1993

[54] FERMENTATION PROCESS FOR THE PRODUCTION OF PYRIMIDINE DEOXYRIBONUCLEOSIDES

[75] Inventors: Russell J. McCandliss, Gaithersburg; David M. Anderson, Rockville, both of Md.

[73] Assignee: Chemgen Corporation, Gaithersberg, Md.

[21] Appl. No.: 448,158

[22] Filed: Dec. 8, 1989

[51] Int. Cl.$^5$ .................. C12N 15/00; C12N 15/70; C12N 15/55; C12P 19/30
[52] U.S. Cl. .................................. 435/89; 435/172.3; 435/252.3; 435/252.33; 435/320.1; 536/23.2; 935/14; 935/60; 935/68; 935/72; 935/73
[58] Field of Search ................... 435/252.3, 252.33, 89

[56] References Cited

FOREIGN PATENT DOCUMENTS 0273660 7/1988 European Pat. Off. ......... 455/172.3

OTHER PUBLICATIONS

Fukui & Tanaka, *Advances in Biochemical Engineering*, 17: 1–35 (1980).
Wang et al. "Uracil-DNA Gylcosylase Inhibitor of Bacteriophage PBS2: Cloning and Effects of Expression of Inhibitor Gene in *Escherichia coli*", *J. Bacteriology*, 1082–1091 (1988).
Aposhian, "A dTMPase Found After Infection of *Bacillus subtilis* with Phage SP5C," Biochem. and Biophys. Res. Comm., vol. 18, No. 2 (1965) pp. 230–235.
Aposhian & Tremblay, "Purification and Properties of an Enzyme Found After Infection of *Bacillus subtilis* with Phage SP5C," Journal of Biological Chemistry, vol. 241, No. 21 (1966), pp. 5096–5101.
Beckwith et al., "Coordination of the Synthesis of the Enzymes in the Pyrimidine Pathway of *E. coli*," J. Mole. Biol. (1962), pp. 618–634.
Bethell & Jones, "Molecular Size and Feedback-Regulation Characteristics of Bacterial Aspartate Transcarbamylases," Archives of Biochem. and Biophys., vol. 134 (1969), pp. 352–365.
Haslam et al., "Inhibition of Thymidylate Synthetase in Bacteriophage Infected *Bacillus subtilis*," Biochim, Biophys. Acta., vol. 134 (1967) pp. 312–326.
Hayward, "Inhibition of Bacerial DNA and Protein Synthesis in *Bacillus subtilis* by Phage SP82. Effect of Changes of Temperature on the Inhibition," Virology, vol. 38 (1969), pp. 538–549.
Hemphill & Whiteley, "Bacteriophages of *Bacillus subtilis*," Bacteriological Review, vol. 39 (1975), pp. 357–315.
Kunkel et al., "Rapid and Efficient Site-Specific Mutagenesis Without Phenotypic Selection," Methods in Enzymology, vol. 154 (1987), pp. 367–382.
Landick & Yanofsky, "Transcription Attenuation," *E. Coli* and *Salmonella Typhimurium* Cellular & Molecular Biology, vol. 2, pp. 1276–1301.
Lerner & Switzer, "Cloning and Structure of the *Bacillus subtilis* Aspartate Transcarbamylase Gene (pyrB)," Journal of Biological Chemistry, vol. 261, No. 24 (1986), pp. 11156–11165.
Lerner et al., "Structure of the *Bacillus subtilis* Pyrimidine Biosynthetic (pyr) Gene Cluster," Journal of Bacteriology (May, 1987), pp. 2202–2206.
Munch-Petersen, "Nucleoside Catabolism," Metabolism of Nucleotides, Nucleosides and Nucleobases in Microorganisms (1983), pp. 203–258.
Neuhard, "Regulation of Pyrimidine Nucleotide Biosynthesis in *Escherichia coli* and Salmonella Typhimurium," The Molecular Biology of Bacterial Growth, pp. 173–184.
Neuhard & Nygaard, "Purines and Pyrimidines," Biosynthesis and Conversions of Nucleotides (1987), pp. 445–473.
Nishihara et al., "The Deoxycytidylate Deaminase Found in *Bacillus subtilis* Infected with Phage SP8," Biochem., vol. 6, No. 7 (1967), pp. 1877–1886.
O'Donovan & Neuhard, "Pyrimidine Metabolism in Microorganisms," Bacteriological Reviews, vol. 34, No. 3, (1970), pp. 278–343.
Paulus & Switzer, "Characterization of Pyrimidine-Repressible and Arginine-Repressible Carbamyl Phosphate Synthetases from *Bacillus subtilis*," Journal of Bacteriology, vol. 137, No. 1 (1979), pp. 32–91.
Potvin, et al., "Pyrimidine Biosynthetic Pathway of *Bacillus subtilis*," Journal of Bacteriology, vol. 123 (1975), pp. 604–615.
Roland, et al., "Role of Translation and Attenuation in the Control of pyrBI Operon Expression in *Escherichia coli* K-12," Journal of Bacteriology, vol. 163, No. 3 (1985), pp. 991-999.

Roscoe & Tucker, "The Biosynthesis of a Pyrimidine Replacing Thymine in Bacteriophage DNA," Biochem., and Biophys. Res. Comm., vol. 16, No. 2 (1964), pp. 106-110.

Roscoe & Tucker, "The Biosynthesis of 5-Hydroxymethyldeoxyuridylic Acid in Bacteriophage-Infected *Bacillus subtilis*," Virology, vol. 29 (1966), pp. 157-166.

Rowlands, "Industrial Strain Improvement: Mutagenesis and Random Screening Procedures," Enzyme Microb. Technol., vol. 6 (1984), pp. 3-10.

Shepherdson & Pardee, "Production and Crystallization of Aspartate Transcarbamylase," Journal of Biol. Chem., vol. 235, No. 11 (1960), pp. 3233-3237.

Takahashi & Marmur, "Replacement of Thymidylic Acid by Deoxyuridylic Acid in the Deoxyribonucleic Acid of a Transducing Phage for *Bacillus subtilis*," Nature, vol. 197 (1963), pp. 794-795.

Thelander & Reichard, "Reduction of Ribonucleotides," Ann. Rev. Biochem., vol. 48 (1979), pp. 133-158.

Turnbough et al., "Attenuation Control of pyrBI Operon Expression in *Escherichia coli* K-12," Proc. Natl. Acad. Sci. USA, vol. 80 (1983), pp. 368-372.

Yakobsen & Guiney, "Conjugal Transfer of Bacterial Chromosomes Mediated by the RK2 Plasmid Transfer Origin Cloned into Transporon Tn5," Journal of Bacteriology, vol. 160, No. 1 (1984), pp. 451-453.

Nowlan, S. F., et al., 1985, The Journal of Biological Chemistry, 260(27):14712-14716.

Levin, H. L., et al., 1985, Proceedings of the National Academy of Sciences USA 82:4643-4647.

Fauve, M., et al., 1989, European Journal of Biochemistry 179:345-358.

Nowlan, S. F., et al., 1983, *Molecular and General Genetics*, 192:264-271.

Jensen, K. F., 1988, *European Journal of Biochemistry*, 175:587-593.

Turnbrough, Jr., C. L., 1983, Journal of Bacteriology, 153:998-1007.

Navre, M., et al., 1983, Proceedings of the National Academy of Sciences USA, 80:1207-1211.

Jensen, K. F., et al., 1982, The EMBO Journal 1(1):69-74.

Miyagawa, K., et al., 1989, Bio/Technology 7:821-824.

Miyagawa, K., et al., 1986, Bio/Technology 4:225-228.

Matsui, H., et al., 1977, Applied and Environmental Microbiology 34(4):337-341.

*Primary Examiner*—Robert A. Wax
*Assistant Examiner*—William W. Moore
*Attorney, Agent, or Firm*—Foley & Lardner

[57] ABSTRACT

DNA coding for at least one enzyme that causes the accumulation of a pyrimidine deoxyribonucleoside is used, in conjunction with metabolic mutations or heterologous DNA coding for metabolic enzymes that also increase pyrimidine deoxyribonucleoside production, to engineer cultured cells to express a pyrimidine deoxyribonucleoside (PdN) in recoverable quantities, providing a commercially useful fermentation source for PdNs.

20 Claims, 14 Drawing Sheets

FIG. 3

N-TERMINUS

```
Met Phe Ser Ile Lys Glu Pro Phe Ser Ile Val Thr Asp
ATG TTT TCT ATC AAA GAA CCT TTT TCT ATC GTC ACC GAC
        C   C   T   G   G   C   C   C   T   T   T   T
        A   A               A       A   A   A   A   A
            G                   G       G   G   G
        AGC                         AGC
          T                           T
```

```
Ser Asp Glu Val Leu Thr Asp Ile           C-TERMINUS
TCT GAC GAA GTC TTA ACC GAC ATC
 C   T   G   T   G   T   T   T
 A           A CTT   A       A
 G           G   C   G
AGC              A
  T              G
```

FIG. 4

OLIGONUCLEOTIDE PROBE mix 1 (48)

```
Met Phe Ser Ile Lys Glu Pro
ATG TTT AGC ATC AAA GAA CC
        C   T   G   G
            T
            A
```

OLIGONUCLEOTIDE PROBE mix 2 (96)

```
Met Phe Ser Ile Lys Glu Pro
ATG TTT TCT ATC AAA GAA CC
        C   C   T   G   G
            A   A
                G
```

FIG. 7a

```
          -130        -120        -110        -100         -90         -80
            *           *           *           *           *           *
          AAA TAC TAG AAA CAA CTA AAC GGA CAC AAT TTC CAA CCA ATA TCT TAA CAT TCT AAA

-70         -60         -50         -40         -30
            *           *           *           *           *
          AGC ATT TAT ATT ATT AGA ATA TAA TGG TAT TAT TCT AAT ATT CCT TCG TGC ATA TTA

-20         -10          1          10          20          30
   *           *           *           *           *           *
  TAA TTA CAG GGA GAG GAT TTA ATG TTT TCT ATT AAA GAA CCA TTT TCA ATT GTT ACA
                                  Met Phe Ser Ile Lys Glu Pro Phe Ser Ile Val Thr 40          50          60          70          80          90
   *           *           *           *           *           *
  AAC TGC GAT GAG GTA TTA ACT GAC ATT AGT CCT TTA TGG GTT CAT AAG ATT CAG CAA
  Asn Cys Asp Glu Val Leu Thr Asp Ile Ser Pro Leu Trp Val His Lys Ile Gln Gln 100         110         120         130         140         150
   *           *           *           *           *           *
  AAT GCT GAT TAT TTT GGA AAA TAC TTT GAT TTA AGT AAA CTA GAA GGA TTG GAA TTT
  Asn Ala Asp Tyr Phe Gly Lys Tyr Phe Asp Leu Ser Lys Leu Glu Gly Leu Glu Phe 160         170         180         190         200
               *           *           *           *           *
  GGT ACA TTT GAA CAT TAT CAA ACA GTA CTA TCA CGA CCA GAA TTT CAT TTA AAT AAA
  Gly Thr Phe Glu His Tyr Gln Thr Val Leu Ser Arg Pro Glu Phe His Leu Asn Lys 210         220         230         240         250         260
   *           *           *           *           *           *
  TGG CTA AGA AAA GAA AAT CTT GTA TTA TCA GAT GAA GAA GAA AAA GAA TTA TTT GAA
  Trp Leu Arg Lys Glu Asn Leu Val Leu Ser Asp Glu Glu Glu Lys Glu Leu Phe Glu 270         280         290         300         310         320
   *           *           *           *           *           *
  AGA TTT TAT TCG TTA TAT GAT AAT GAT GAA TTT TAT GAA GAT TGT ATG CCA ACT AAA
  Arg Phe Tyr Ser Leu Tyr Asp Asn Asp Glu Phe Tyr Glu Asp Cys Met Pro Thr Lys 330         340         350         360         370
               *           *           *           *           *
  ATG TGT GAA GGA ATT TAT AAA TTA TCA TTA CAA AAA TTC GTA GAT AAA ATC TAT GTT
  Met Cys Glu Gly Ile Tyr Lys Leu Ser Leu Gln Lys Phe Val Asp Lys Ile Tyr Val 380         390         400         410         420         430
   *           *           *           *           *           *
  GTA ACA AGA ACA AGT GAA GGA ACC AAA GAA GGA AAA AGA AAA TTT ATT GAA ACT TTC
  Val Thr Arg Thr Ser Glu Gly Thr Lys Glu Gly Lys Arg Lys Phe Ile Glu Thr Phe
```

FIG. 7b

```
      440         450         460         470         480         490
       *           *           *           *           *           *
TTA AAT TCT AAT AAA GTA GAG ATT ATT TTT GTT GGG AAA AAT GAA AAG AAA TCA GAT
Leu Asn Ser Asn Lys Val Glu Ile Ile Phe Val Gly Lys Asn Glu Lys Lys Ser Asp 500         510         520         530         540
           *           *           *           *           *
TAT ATT AAG AAT CTA AAG AAT GTA AAA ATG ATT GTA GAA GAT GAA TTA TCA AAT ATT
Tyr Ile Lys Asn Leu Lys Asn Val Lys Met Ile Val Glu Asp Glu Leu Ser Asn Ile 550         560         570         580         590         600
  *           *           *           *           *           *
AAT GAT ATT GTA GAA AAT TGT AAT GAT GGT TTT GAA GAA GTA GAT ATT TAT ATT CCA
Asn Asp Ile Val Glu Asn Cys Asn Asp Gly Phe Glu Glu Val Asp Ile Tyr Ile Pro 610         620         630         640         650         660
    *           *           *           *           *           *
TCA ACT GGT TAT AAC AAT AAA GAT ATT GAT GGT TTT AAT GAA AAT CTA ATG AAA AAA
Ser Thr Gly Tyr Asn Asn Lys Asp Ile Asp Gly Phe Asn Glu Asn Leu Met Lys Lys 670         680         690         700         710         720
           *           *           *           *           *           *
GGA TTT AAT GCC GTT CCA TAT GTA ATT ATA GAA AGA CCA GAA ACA GAA GAG AAA GCA
Gly Phe Asn Ala Val Pro Tyr Val Ile Ile Glu Arg Pro Glu Thr Glu Glu Lys Ala 730         740         750         760         770
                *           *           *           *           *
GTA TAA AAT GAC ATA AGA GAC TTA TAA GTC TCT TAT GTT TTT ATT TTT TGT CTA CAA
Val ---

780         790         800         810         820         830
            *           *           *           *           *           *
AGG AGA GAA TAA GAT GAA TCC ATC TAG TCA ATT AAA TCC TGC TAA TCC AAC AAG TCC 840         850         860         870         880         890
            *           *           *           *           *           *
TTT AAA TCC TAC CAG TCC AAA TAA TTT ATT AAG TCC TAC ACA TCC TGT TAA CTA CCT 900         910         920         930         940
            *           *           *           *           *
CTA TGA AGA TGA TAA AAG TAG TAC AAT TCT TCA TTT AAG TGA TCC TAT TAT ATA GAT 950         960         970         980         990         1000
       *           *           *           *           *           *
TCC CTT TGG AAT TAT TTT AAT AAT CAT TAT TAT TTT ATT TTA TCT TTT ATT TAA AGA
```

FIG. 7c

```
      1010         1020         1030         1040         1050         1060
       *            *            *            *            *            *
ATT ATA AAA TTT GAG AAA CAA AAC TAT ATA AAT ATT AAA TAG AAA TGG GAA AAA TAA 1070         1080         1090         1100         1110
            *            *            *            *            *
TGG GAA GAG AGA ATG AAC AAT ATA ATA TTG AAG AAG CAA AAA GTT AAT TGG AGA GAC 1120         1130         1140         1150         1160         1170
   *            *            *            *            *            *
TGA TCT GTC TTA TTC TGA TAT TTC TAA AAA GAC TGG GGT AAA ATA TCA AAC AGT ACA 1180         1190         1200         1210         1220         1230
        *            *            *            *            *            *
ATA TCA TGG TTC AAA AAT TAG AGG TAA GAG ACC ACG AAA AGA AAG TAT GCA TGG TGA 1240         1250         1260         1270         1280         1290
            *            *            *            *            *            *
GGT AAT CAC TAG AAA AAT GAC TCC AGA AGA AGA AAT TAG ATA TGG AGT TAG AAA ACC 1300         1310         1320         1330         1340
                *            *            *            *            *
TTT AAA TTA TAC AGA AGA AAA GGA TAA TGT AAA GGG AAT TAC ACC AAC TCA CAT AGT 1350         1360         1370         1380         1390         1400
       *            *            *            *            *            *
TAA TGA ATC TTT AAA TAA ACC AAT TGA AAA GAA ATT TGA TAG TGG TTC TAT AAG TTT 1410         1420         1430         1440         1450         1460
            *            *            *            *            *            *
AAA CAT CCA AGA TAT TAA TAT TGA CAA TAT TGA TGA ACA ATT TGA AAG AAT TAA AAA

1470
                *
         TAC TAT TAA AAG CTT
```

```
AY006-
       |<--rbs-->|        EcoRI
5'- CCT CTC CCT GGA ATT CTA ATA TGC ACG -3'
```

```
dTMPase -                              |<--rbs-->|    dTMPase
                                                      |--->
   -40       -30        -20        -10         1
    *         *          *          *          *
5' AT ATT CCT TCG TGC ATA TTA TAA TTA CAG GGA GAG GAT TTA ATG TTT

3'- GC ACG TAT AAT CTT AAG GTC CCT CTC C - 5'   AY006
```

FIG. II

FERMENTATION PROCESS FOR THE PRODUCTION OF PYRIMIDINE DEOXYRIBONUCLEOSIDES

BACKGROUND OF THE INVENTION

The present invention relates to microbial fermentation processes that utilize genetically-modified bacterial or yeast cells (microbial) to produce a pyrimidine deoxyribonucleoside (PdN) in recoverable quantities.

Pyrimidine deoxyribonucleosides, such as thymidine (TdR) and deoxyuridine (UdR), are commercially useful starting compounds for the production of antiviral compounds comprising synthetic analogs of pyrimidines, such as azidothymidine (AZT) or azidodeoxyuridine (AZdU). For example, thymidine and deoxyuridine (UdR) are currently produced by organic synthesis utilizing a multi-step process which is very costly. Thus the high cost of thymidine has contributed to the high cost of antiviral therapeutics, e.g., the resulting high price of the drug AZT. There have not been any alternative methods, however, for obtaining thymidine or other PdNs suitable for use in producing antiviral therapeutics such as AZT. Thus, there is a longstanding and urgent need for a less expensive method for the production of commercially useful quantities of PdNs.

Exemplary of PdNs are thymidine and deoxyuridine, which are composed of the bases thymine and uracil, respectively, covalently attached at their 1-nitrogen to the 1'-carbon of the sugar 2-deoxyribose. These nucleosides normally exist in cells as mono-, di- or trinucleotides. Thymidine functions primarily as a component of DNA. In most cells of microorganisms and eukaryotic organisms, PdNs are products of the de novo pyrimidine biosynthetic pathway.

Analysis of PdN biosynthetic pathways. In order to provide an alternative, less expensive method for PdN production, the analysis of the metabolic pathways of PdN de novo synthesis might provide useful information as to possible cell mutants that could produce a PdN by the use of microbial fermentors or cell culture bioreactors. Pyrimidines, pyrimidine nucleosides, and pyrimidine nucleotides are synthesized from aspartic acid and carbamoyl phosphate (derived from glutamine and $CO_2$) by way of a multi-step pathway, which is shown in FIG. 1. See O'Donovan & Neuhard, *Bacteriol. Rev.* 34:278-343 (1970), the contents of which are herein incorporated by reference. The enzymes of the pathway, indicated in FIG. 1 by the *E. coli* gene symbols, are listed below:

pyrA or carAB—Carbamoyl phosphate synthase (EC 6.3.5.5)
pyrBI—Aspartate transcarbamoylase (EC 2.1.3.2)
pyrC—Dihydroorotase (EC 3.5.2.3)
pyrD—Dihydroorote oxidase (EC 1.3.3.1)
pyrE—Orotate phosphoribosyltransferase (EC 2.4.2.10)
pyrF—Orotidine 5'-phosphate decarboxylase (EC 4.1.1.23)
pyrG—Cytidine triphosphate (CTP) synthase (EC 6.3.4.2)
pyrH—Nucleoside-phosphate kinase (EC 2.7.4.4)
ndk—Nucleoside diphosphate kinase (EC 2.7.4.6)
nrd—Ribonucleoside diphosphate reductase (EC 1.17.4.1)
dcd—Deoxycytidine triphosphate (dCTP)-deaminase (EC 3.5.4.13)
dut—Deoxyuridine triphosphate nucleotide hydrolase (dUTPase) (EC 3.6.1.23)
thyA—Thymidylate synthase (EC 2.1.1.45).

The endproducts of the pathway can be generally defined as uridine triphosphate (UTP), cytidine triphosphate (CTP), deoxycytidine triphosphate (dCTP) and thymidine triphosphate (TTP), all of which function as building blocks for RNA or DNA as well as for other cellular components. Because of the large number of endproducts, energy requirements and enzymatic steps in this pathway, de novo biosynthesis of pyrimidines has many regulated steps. See, e.g., Neuhard, In THE MOLECULAR BIOLOGY OF BACTERIAL GROWTH, Jones & Bartlett, Boston (1985) at pages 173-184.

Regulation of the pyrimidine de novo biosynthetic pathway. The enzymatic steps of the pyrimidine de novo biosynthetic pathway are regulated in vivo by (A) feedback inhibition of key enzymes by the concentration of the endproducts or other metabolites (either alone or in concert); and (B) repression and/or attenuation of enzyme synthesis. Beckwith et al, *J. Mol. Biol.* 5:618-634 (1962); Potvin et al, *J. Bacteriol.* 123:604-615 (1975); Roland et al, *J. Bacteriol.* 163:991-999 (1985). This pathway in bacteria has been studied in detail. Neuhard & Nygaard, In *ESCHERICHIA COLI AND SALMONELLA TYPHIMURIUM,* CELLULAR AND MOLECULAR BIOLOGY, American Society for Microbiology, Washington, D.C. (1987), at pages 445-473.

According to Neuhard, id., the key regulatory enzymes of pyrimidine biosynthesis are carbamoyl phosphate synthase (pyrA or carAB), aspartate transcarbamoylase (pyrBI), CTP synthase (pyrG) and deoxycytidine triphosphate deaminase (dcd). Carbamoyl phosphate synthase activity is inhibited by uridine nucleotides and its synthesis is cumulatively repressed by arginine and uracil. Regulation by arginine is necessary because carbamoyl phosphate is an intermediate in the biosynthesis of arginine as well as pyrimidines. In *E. coli* a specific repressor protein, argR, has been identified. In *Bacillus subtilis* two carbamoyl phosphate synthase isoenzymes have been identified (Paulus & Switzer, *J. Bacteriol.* 137:82-91 [1978]). One is specifically regulated by arginine and the other by pyrimidines (primarily uracil derivatives).

Aspartate transcarbamoylase (AT) catalyzes the first committed step in pyrimidine biosynthesis and is therefore subject to metabolic regulation by pyrimidines. The enzyme AT consists of two types of subunits, the catalytic subunits (pyrB), and the regulatory subunits (pyrI). The activity of AT is subject to allosteric inhibition by CTP, one of the endproducts of the pathway, and activation by adenosine triphosphate (ATP), whose concentration is dependent upon of the energy state of the cell. The level of AT present in the cell is apparently regulated by CTP and UTP. The encoding gene and associated regulatory regions have been cloned and their DNA sequences determined. See Landick & Yanofsky, In *ESCHERICHIA COLI AND SALMONELLA TYPHIMURIUM,* CELLULAR AND MOLECULAR BIOLOGY, 1276-1301; Roland & Powell, supra: and Turnbough et al, *Proc. Nat'l Acad. Sci. USA* 80:368-72 (1983).

Constitutive *E. coli* mutants have been described in which the level of AT was elevated about 30-fold over normally repressed levels. However, there have also been experiments described in which starvation of an *E.*

*coli* pyrimidine auxotroph for pyrimidines resulted in about a 1000-fold increase in the level of the AT enzyme (Shepherdson & Pardee, *J. Biol. Chem.* 235:3233-37 [1960]). Thus, the range of enzyme levels is very great and depends on the levels of the end products in the cell and, under normal, repressed conditions, the enzyme is present at much lower levels than are possible under fully-deregulated conditions.

The regulation of AT in *B. subtilis* differs from that in *E. coli* and *S. typhimurium* in that no in vitro activation or inhibition of enzyme activity has been demonstrated (Bethell & Jones, *Arch. Biochem. Biophys.* 134:352-65 [1969]). There is, however, regulation of enzyme synthesis by uracil, probably by an attenuation mechanism similar to that proposed for the other organisms. Lerner & Switzer, *J. Biol. Chem.* 261:11156-65 (1986).

The third key enzyme is CTP synthase (pyrG) which catalyzes the amination of UTP to form CTP. The enzyme from *E. coli* is subject to complex allosteric regulation. In vitro studies demonstrate stimulation by GTP, ATP, and UTP. The mechanism of its genetic regulation is not known. The fourth key enzyme is dCTP deaminase, which catalyzes the deamination of dCTP to dUTP. The substrate dCTP is a branch point compound since it is either incorporated into DNA or used as the precursor for TTP synthesis. The enzyme dCTP deaminase is subject to feedback inhibition by TTP. In *B. subtilis* dCTP or dCDP is converted to dCMP, which is then utilized as the substrate for dCMP deaminase, producing dUMP as the product. However, dUMP does not accumulate in the cell because it is immediately converted to TMP by the enzyme thymidylate synthase. Munch-Petersen, ed., METABOLISM OF NUCLEOTIDES, NUCLEOSIDES AND NUCLEOBASES IN MICROORGANISMS, Academic Press, 149-201 (1983). The enzyme dCMP deaminase is subject to allosteric activation by dCTP and inhibition by TTP.

Another enzyme, ribonucleoside diphosphate reductase (nrd), plays a key role in the biosynthesis of pyrimidine deoxyribonucleotides and is subject to complex regulation. Thelander & Reichard, *Ann. Rev. Biochem* 48:133-58 (1979). This enzyme catalyzes the reduction of ribonucleoside diphosphates to deoxyribonucleoside diphosphates and acts on both purine and pyrimidine nucleotides. However, most inhibition studies have been performed on purified enzyme and may not truly reflect the situation in vivo, since the enzyme is normally membrane-associated. The level of enzyme activity generally seems to be a function of the total nucleotide concentration in the cell, as well as the rate of DNA synthesis.

In *E. coli* and *S. typhimurium*, the pyrimidine biosynthetic genes are scattered throughout the chromosome and do not constitute an operon (Beckwith, supra; Neuhard, In THE MOLECULAR BIOLOGY OF BACTERIAL GROWTH, supra, (1985) at pages 173-84) except for the subunits of carbamoyl phosphate synthase (carA and carB) and the subunits of aspartate transcarbamoylase (pyrB and pyrI). As mentioned above, their expression appears to be regulated at the level of transcription by an attenuation mechanism, which is dependent upon the intracellular concentrations of CTP and UTP. Any situation in which the levels of CTP or UTP are low will result in increased expression of these enzymes.

To date no specific repressor protein acting on the pyrimidine biosynthetic genes has been discovered and coordinate expression of the genes has not been seen. In *B. subtilis*, the genes pyrA, pyrBI, pyrC, pyrD, pyrE, and pyrF are located close to one another on the chromosome (Lerner et al, *J. Bacteriol.* 169:2202-06 (1987), the contents of which are herein incorporated by reference) and are expressed at very low levels when the organism is grown in the presence of uracil (Potvin et al, *J. Bacteriol.* 123:604-15 [1975]), but the evidence so far also points to regulation by an attenuation mechanism (Lerner, supra, 1986). There is no clear evidence for an operon type of gene organization, nor for the existence of a repressor protein.

Lack of accumulation of pyrimidine deoxyribonucleosides. The enzyme reactions which involve a representative PdN (thymidine) are shown in FIG. 2. In a wild type cell growing under non-starvation conditions, thymidine is not present or exists at very low levels because the precursor deoxyuridine monophosphate (dUMP) is converted directly to thymidine monophosphate (TMP) and then to thymidine diphosphate (TDP) and thymidine triphosphate (TTP). Since thymidine is present primarily in the form of TTP, a building block for DNA, it is normally utilized as rapidly as it is synthesized and does not accumulate, due to regulated biosynthesis. For the same reasons, deoxyuridine also is not normally found in cells. Existing pyrimidine metabolic pathways therefore normally preclude the accumulation of excess deoxyuridine (UdR), dTMP or thymidine (TdR).

Although alternative metabolic mechanisms can result in the synthesis of thymidine, the thymidine is either degraded or used by the cell for synthesis of thymidine nucleotides, thus preventing the accumulation of thymidine. For example, the action of non-specific phosphatases on TMP to produce thymidine does not lead to the accumulation of thymidine because any thymidine produced is either degraded rapidly to thymine and deoxyribose-1-phosphate by the action of thymidine phosphorylase, the product of the deoA gene (Munch-Peterson, supra, 203-58), or phosphorylated by thymidine kinase to produce TMP. In *B. subtilis*, there appears to be only one pyrimidine nucleoside phosphorylase which can use either thymidine or uridine as the nucleoside substrate. This enzyme also functions in the reverse manner, allowing the incorporation of exogenous thymine into thymidine. Many organisms can also take up thymidine and convert it to TMP by the action of thymidine kinase. As a consequence, thymidine does not accumulate via the metabolic pathways existing in organisms. Deoxyuridine produced from dUMP by non-specific phosphatases also serves as a substrate for thymidine kinase, yielding dUMP, or as a substrate for thymidine phosphorylase, yielding uracil and deoxyribose 1-phosphate.

Although there are several examples of production of nucleosides, pyrimidine-like compounds, and related products by fermentation, there is no suggestion that PdN production could be obtained in a similar manner, since in these cases mutations of existing pathways provided accumulation of the desired pyrimidine or pyrimidine ribonucleoside, but did not suggest or provide for the accumulation of pyrimidine deoxyribonucleosides. See, e.g., Konishi, *Chem. Abs.* 70:18917j (1969); Nakayama, *Chem. Abs.* 84:119951k (1976); and Nakayama, *Chem. Abs.* 89:74214g, 88:119441b, 88:19442c (1978).

Indeed, such a mutation, or other metabolic mechanisms described above, could not provide for commercially useful amounts of thymidine or deoxyuridine to accumulate because of the above-mentioned removal of thymidine (or deoxyuridine) by either TMP (or dUMP) synthesis or degradation to thymine (or uracil) and deoxyribose-1-phosphate. Because the regulatory mechanisms for the pyrimidine biosynthetic genes appear to be primarily attenuation mechanisms, with each gene individually regulated, it would not be expected or predictable that mutants highly de-repressed for the whole pathway could be generated, resulting in the accumulation of specific PdNs in recoverable amounts. Also, it has not been possible heretofore to exploit existing metabolic pathways in any organism to accomplish practical PdN production by rapid and specific irreversible hydrolysis of TMP to thymidine or dUMP to deoxyuridine, as the former is formed in vivo. This has followed from the fact that the equilibrium of the thymidine kinase reaction is unfavorable for TdR or UdR production.

Accordingly, no approach has been available that provided or suggested a solution to the problem of producing commercially useful amounts of PdN at relatively low cost. Moreover, known means of modification of existing metabolic pathways have not provided for the accumulation of recoverable amounts of PdNs such as TdR during microbial fermentation, due to extensive regulation and unfavorable reaction equilibria in relevant synthetic steps. Thus a need exists to solve the problem of commercial production of recoverable quantities of a PdN.

SUMMARY OF THE INVENTION

It is therefore an object of the present invention to provide a genetically-modified microbial cell that produces commercially useful amounts of PdNs from a carbon source. In this regard, a "genetically modified cell" is a cell, or the progeny of a cell, reflecting a modification effected by transformation with heterologous DNA which codes for a protein or by treatment with a chemical or physical mutagen.

It is also an object of the present invention to provide a process for the fermentative production of a PdN from a carbon source.

In accomplishing the foregoing objects, there has been provided, in accordance with one aspect of the present invention, a replicatable microorganism that comprises and expresses a DNA sequence encoding a pyrimidine deoxyribonucleotide phosphohydrolase (PdNPase) that converts a PdN monophosphate to a pyrimidine deoxyribonucleoside. In certain preferred embodiments, the PdNPase-encoding DNA sequence codes for thymidylate phosphohydrolase, and the microorganism expresses recoverable amounts of thymidine or deoxyuridine.

In accordance with another aspect of the present invention, a microbial culture is provided that consists essentially of microorganisms, as described above, that express a DNA sequence encoding a PdNPase, wherein the culture, upon metabolizing a carbon source, accumulates a PdN in recoverable amounts. The qualifier "consisting essentially of" means, in this context, that a microbial culture of the present invention, while possibly including cells that do not express a PdNPase-encoding DNA, does not contain so many such cells that its salient property—the production of recoverable amounts of a PdN—is adversely affected.

A process has also been provided, in accordance with another aspect of the present invention, for the fermentative production of a PdN from a carbon source, comprising the steps of (A) providing a fermentation reactor containing culture medium which comprises the source of carbon; (B) adding to the reactor a microbial culture producing a PdN in recoverable amounts; then (C) establishing and maintaining conditions within the reactor such that the source of carbon is fermented by the microbial culture to accumulate a PdN in the culture medium; and (D) recovering the PdN from the reactor. The PdN obtained from step (D) can be recovered from medium at a PdN concentration of at least 1 g/L, preferably at least about 30 g/L and especially about 70 g/L or more.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention is illustrated in the accompanying drawings, in which:

FIG. 3 is a diagram depicting the N-terminal amino-acid sequence of thymidylate phosphohydrolase and corresponding nucleic acid encoding sequences.

FIG. 4 is a diagram depicting the alternative probe sequences of both oligonucleotide mixes used to isolate dTMPase-encoding nucleic-acid sequences.

FIGS. 7A, 7B and 7C present a representative dTMPase encoding DNA sequence, including flanking DNA sequences, as obtained from a PBSI bacteriophage.

DETAILED DESCRIPTION OF THE PREFERRED EMBODIMENTS

Figure 1:
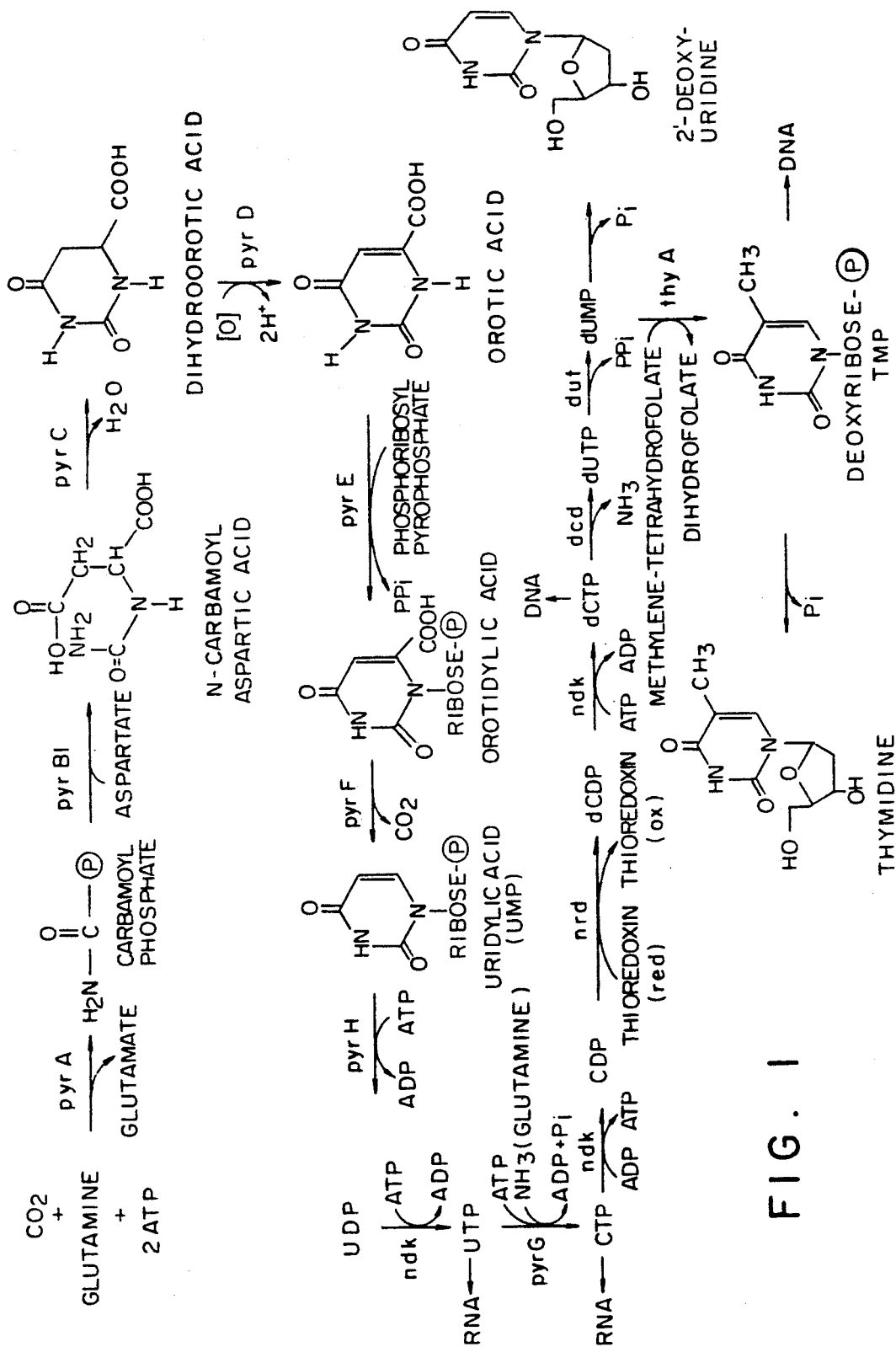
FIG. 1 is a diagram depicting pyrimidine biosynthetic pathways.
Figure 2:
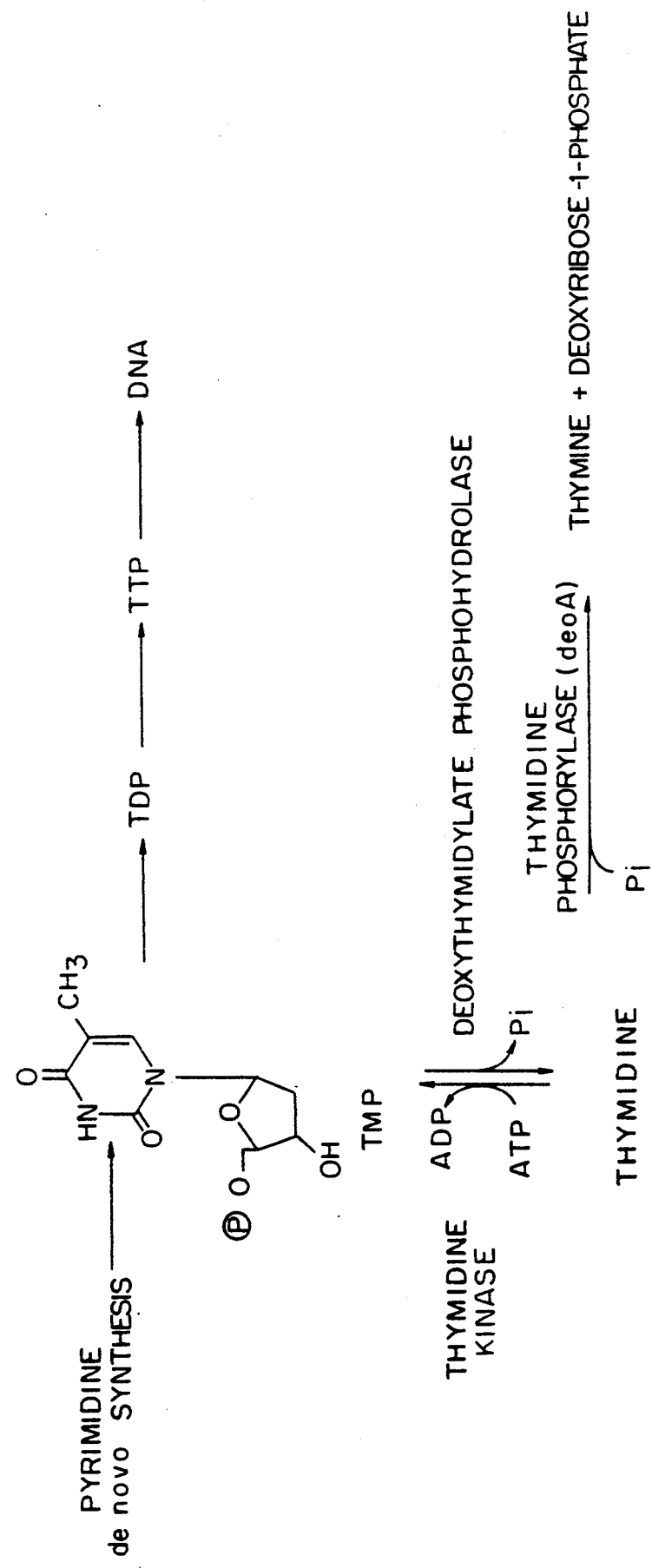
FIG. 2 is a diagram depicting the biochemical reactions of thymidine.

It has been discovered that a recombinant microbial cell can be used, in a fermentation process, as a source for commercial quantities of PdNs. In particular, an additional enzymatic step can be added, via recombinant techniques, to the pyrimidine deoxyribonucleoside de novo biosynthetic pathway of microbial cells, resulting in accumulation of a desired PdN, and the recombinant cells thus obtained can be further modified to assure the production of commercially useful amounts of PdN. In this regard, a "commercially useful" amount of a PdN is associated with a production level of PdN that can be accommodated by state-of-the art extraction or other product recovery technology.

The transformation effected in accordance with the present invention employs a cloned (heterologous) DNA encoding an enzyme that converts pyrimidine deoxyribonucleoside monophosphates to PdNs, i.e., a PdNPase. Cells engineered to express such an enzyme are further modified by the introduction of a metabolic mutation, or heterologous DNA coding for a metabolic enzyme or enzyme modulator, that enhances PdN production. Surprisingly, the latter manipulation of a cell transformed with a DNA sequence encoding a PdNPase enables the fermentative production of PdNs without killing the transformed cell before useful quantities of PdNs can be recovered.

Foreign DNA suitable for transforming a microbial cell in accordance with the present invention can be obtained from uracil-containing viruses, as well as from other replicatable organisms and viruses that utilize uracil or hydroxymethyluracil, instead of thymine, in synthesizing DNA. This group of organisms and viruses produce a PdNPase enzyme exemplified by thymidylate phosphohydrolase (dTMPase), such as that designated EC 3.1.3.35, which converts either TMP to thymidine or dUMP to deoxyuridine.

Illustrative of the group are the known bacteriophages PBS1 and PBS2, which are readily available, e.g., from the Bacillus Genetic Stock Center, Ohio State University (Columbus, Ohio). Both of these phages infect *B. subtilis* and express the enzyme dTMPase. Hemphill & Whiteley, *Bacteriol. Rev.* 39:257-315 (1975). PBS1 and its clear-plaque variant PBS2 contain uracil in their DNA in place of thymine. Takahashi & Marmur, *Nature* 197:794-95 (1963). Other examples of bacteriophages that express dTMPase enzymes include the Bacillus phages SP8 and SP5C, available commercially from the American Type Culture Collection (Rockville, Md.), among other sources. See also Nishara et al, *Biochemistry* 6:1877 (1967); Aposhian, *Biochem. Biophys. Res. Comm.* 18:230 (1965); and Aposhian & Tremblay, *J. Biol. Chem.* 241:5095 (1966). (Unless otherwise indicated, the documents cited in this paragraph and in the remainder of this detailed description are hereby incorporated by reference.)

For the purpose of modifying a microbial cell of the present invention, thereby to produce recoverable amounts of a PdN, a gene encoding a PdNPase is cloned and introduced into a suitable host cell such that the cloned enzyme is expressed in sufficient quantities to catalyze the conversion of a PdN monophosphate to recoverable amounts of a PdN. The host cell thus transformed is additionally altered, using conventional mutation or recombinant techniques further to modify the PdN synthetic pathway, such that a commercially useful amount of a PdN is produced and recovered. An example of such a cell is *E. coli* strain CMG 1128 (see Example 11, below), which produces recoverable amounts of the PdN, thymidine.

Thus, in accordance with the present invention, a PdNPase is introduced by recombinant techniques into a microbial cell, along with mutations or additional metabolic gene-encoding DNA, such that a PdN, e.g., thymidine, is not utilized by thymidine kinase to make TMP nor by thymidine phosphorylase to make thymine and deoxyribose-1-phosphate, resulting in the accumulation of a recoverable amount of a thymidine.

Alternatively, deoxyuridine can accumulate in the medium of a culture of a microorganism of the present invention, in addition to transformation with a PdNPase-encoding DNA, by introduction of a thymidylate synthase mutation that prevents the formation of TMP from dUMP, thereby increasing the accumulation of dUMP. The accumulation of dUMP provides a suitable substrate for the PdNPase to produce the PdN, deoxyuridine. Such an organism would need an additional source of thymidine for growth. Alternatively, the inhibition of thymidylate synthase can be effected by the use of a temperature sensitive enzyme or the regulated expression of a gene encoding a thymidylate synthase inhibitor, e.g., obtained from a hydroxymethyluracil-containing Bacillus bacteriophage, such as phages phiE, SP82G or SP8 using conventional procedures. See Haslam et al, *Biochem. Biophys. Acta* 134:312 (1967); Hayward, *Virology* 38:538 (1969); Roscoe & Tucker, *Biochem. Biophys. Res. Comm.* 16:106 (1964); and Roscoe & Tucker, *Virology* 29:157 (1966). When production of deoxyuridine is desired, the thymidylate synthase activity may be disabled and the dUMP can then be converted to deoxyuridine by a PdNPase, such as dTMPase. Thus, a recombinant cell according to the present invention will accumulate a PdN into the medium in recoverable quantities.

Mutations affecting enzymes in the PdN synthetic metabolic pathway that can be used to increase production of a PdN, in accordance with the present invention, include (1) substrate analog- and chemical-resistance mutations, (2) metabolic endproduct-resistance mutations, (3) purine-pyrimidine- and nucleoside-transport mutations and (4) mutations that affect metabolic enzyme activity, among others. PdN-producing cells of the present invention can also be recombined with cloned DNA that codes for pyrimidine metabolic pathway enzymes or enzyme-inhibitory enzymes, thereby promoting increased PdN production by increasing concentrations of rate-limiting enzymes in the pathway or inhibiting rate-limiting enzymes that decrease PdN production.

Conventional techniques are available for introducing suitable mutations into a recombinant cell of the present invention. See, for example, Rowlands, *Enzyme Microb. Technol.* 6:3-10 (1984), and Miller, In EXPERIMENTS IN MOLECULAR GENETICS, Cold Spring Harbor Laboratory, New York (1972). Plasmid and cellular sources for such mutations are commercially available, for example, from the *E. coli* Genetic Stock Center, Yale University (New Haven, Conn., U.S.A.), and the Bacillus Genetic Stock Center, Ohio State University (Columbus, Ohio U.S.A.).

A substrate analog- or chemical-resistance mutations. A substrate analog- or chemical-resistance mutation can be introduced by subjecting a PdN-producing cell of the present invention to conventional chemical or physical mutagenesis, followed by exposure of mutagenized cells to increasing concentrations in the culture medium of a selection agent (that is, the compound to which resistance is sought). Cells which survive, by virtue of a resistance mutation, can then be selected. Alternatively, a plasmid containing one or more genes that confer the desired resistance can be used to transform a PdN-producing cell, thereby increasing PdN production. Plasmid and cellular sources for such mutations are commercially available, from the *E. coli* Genetic Stock Center and from the Bacillus Genetic Stock Center, as mentioned above.

Exemplary of a suitable chemical-resistance mutation is a hydroxyurea resistance mutation whereby the activity or amount of ribonucleotide reductase is enhanced to increase production of a PdN. Another suitable chemical-resistance mutation is one imparting resistance to trimethoprim by means of elevated levels of dihydrofolate reductase, which affects the rate and extent of the conversion of dUMP to TMP by thymidylate synthase, resulting in an increased rate of thymidine production.

Substrate analog-resistance mutations include pyrimidine analog resistant mutations which can be similarly incorporated into a PdN-producing cell, according to the present invention, to increase the accumulation of a PdN. Among the pyrimidine analogs to which resistance mutations can be keyed are thiouracil, 6-azauracil, 5-fluorouracil, 5-fluoroorotic acid, 5-fluorocytidine, 5-fluorodeoxyuridine, 5-fluorodeoxycytidine, 5-fluorouridine, 3'-azidothymidine and pyrimidine-2',3'-dideoxynucleoside, as well asother pyrimidine analogs such as the azidopyrimidines, the cyanopyrimidines as presented in Table 1. These analogs are readily available, for example, from Sigma Chemical Company, St. Louis.

TABLE 1: PYRIMIDINE ANALOGS

N'-Acetylcytidine
3'-O-Acetylthymidine
Adenosine N'-Oxide
Allopurinol Riboside
4-Amino-5-Aminomethyl-2-Methyl-Pyrimidine
1-Aminobarbituric Acid
2-Amino-5-Bromo-6-Methyl Pyrimidinol
4-Amino-5-Carbethoxy-2-Ethyl-Mercaptopyrimidine
5-Amino-6-Carboxy-2,4-Dihydroxy-Pyrimidine
2-Amino-4-Chloro-6-Methyl-Pyrimidine
3'-Amino-3'-Deoxythymidine
5'-Amino-5'-Deoxythymidine
5'-Amino-2'-Deoxyuridine
5'-Amino-2',5'-Dideoxy-5-Iodocytidine
5'-Amino-2',5'-Dideoxy-5-Iodouridine
4-Amino-2',6-Dihydroxy-5-Nitrosopyrimidine
2-Amino-4,6-Dihydroxypyrimidine
4-Amino-2,6-Dihydroxypyrimidine
5-Amino-2,4-Dihydroxypyrimidine
4-Amino-1,3-Dimethyl-2,6-Dioxy-5-Nitrosopyrimidine
2-Amino-4,6-Dimethylpyrimidine
4-Amino-2-Hydroxy-5-Hydroxy-Methylpyrimidine
4-Amino-6-Hydroxy-2-Mercapto-5-Nitrosopyrimidine
4-Amino-6-Hydroxy-2-Mercapto-Pyrimidine
2-Amino-4-Hydroxy-6-Methylpyrimidine
4-Amino-2-Hydroxy-5-Methylpyrimidine
2-Amino-4-Hydroxypyrimidine
4-Amino-2-Hydroxypyrimidine
4-Amino-6-Hydroxy-2-Thiopyrimidine
2-Amino-4-Methylpyrimidine
4-Aminoorotic Acid
4-Amino-2-Thiopyrimidine
6-Amino-2-Thiouracil
5-Amino-2,4,6-Trihydroxypyrimidine
4-Aminouracil
5-Aminouracil
6-Aminouracil
5-Aminouricine Amobarbital
2,3'-Anhydrothymidine
5-Azacytidine
6-Azacytidine
5-Azacytosine
6-Azacytosine
5-Aza-2'-Deoxycytidine
6-Aza-2'-Deoxyuridine
6-Aza-2-Thiothymine
6-Azathymine
5-Azauracil
6-Azauracil Riboside
6-Azauridine
2'-Azido-2'-Deoxycytidine
3'-Azido-3'-Deoxythymidine
2'-Azido-2'-Deoxyuridine
Barbituric Acid
3'-O-Benzoylthymidine
5'-Benxoyluridine
5-Bromocytidine
5-Bromocytosine
5-Bromo-2'-Deoxycytidine
5-Bromo-2,3'-Dideoxyuridine
5-Bromo-2,4-Dihydroxypyrimidine
5-Bromo-2',3'-Isopropylidene-Uridine
5-Bromo-1-Methyluracil
5-Bromoorotic Acid
5-Bromouracil
5-Bromouridine
(E)-5-(2-Bromovinyl)Uridine
3-Butyluracil
5-Carbethoxycytosine
5-Carbethoxy-2,4-Dihydroxypyrimidine
5-Carbethoxy-2-Ethylmercapto-4-Hydroxpyrimidine
5-Carbethoxy-2-Thiouracil
5-Carbethoxyuracil
5-Carboxycytosine
5-Carboxy-2,4-Dihydroxypyrimidine
6-Carboxy-2,4-Dihydroxypyrimidine
5-Carboxy-2-Ethylmercapto-4-Hydroxypyrimidine
5-Carboxy-4-Hydroxy-2-Thiopyrimidine
Carboxymethyluracil
6-Carboxy-5-Nitro-2,4-Dioxypyrimidine
5-Carboxy-2-Thiouracil
5-Carboxyuracil
5-Chlorocytosine Arabinoside
5'-Chloro-5'-Deoxycytidine
2'-Chloro-2'-Deoxy-4-Thiouridine
2'-Chloro-2'-Deoxyuridine
5'-chlorodeoxyuridine
2-Chloro-4,5-Diaminopyrimidine
6-Chloro-2,4-Dimethoxypyrimidine
2-Chloropyrimidine
5-Chlorouracil
4,5-Diamino-2-Chloropyrimidine
4,5-Diamino-2,6-Dihydroxypyrimidine
2,5-Diamino-4,6-Dihydroxypyrimidine
4,6-Diamino-2-Ethylmercaptopyrimidine
4,6-Diamino-5-(Formylamino)-Pyrimidine
4,5-Diamino-6-Hydroxy-2-Mercaptopyrimidine
4,6-Diamino-2-Hydroxy-5-Nitrosopyrimidine 4,5-Diamino-6-Hydroxypyrimidine
2,4-Diamino-6-Hydroxypyrimidine
4,6-Diamino-2-Hydroxypyrimidine
4,6-Diamino-2-Methylmercaptopyrimidine
2,4-Diamino-6-Methyl-5-Nitropyrimidine
4,5-Diamino-6-Methyl-2-Thiopyrimidine
2,4-Diamino-5-Nitropyrimidine
4,5-Diaminopyrimidine
4,5-Diamino-2-Thiopyrimidine
4,5-Diamino-6-Thiopyrimidine
4,6-Diamino-2-Thiopyrimidine
5,6-Diaminouracil
5-Diazo-2'-Deoxyuridine
5-Diazouracil
4,6-Dichloro-5-Aminopyrimidine
2,4-Dichloro-6-Methylpyrimidine
2,4-Dichloropyrimidine
4,6-Dichloropyrimidine
2',3'-Dideoxycytidine
2',3'-Dideoxyuridine
2,4-Diethoxypyrimidine
5,6-Dihydrodeoxyuridine
5,6-Dihydro-2,4-Dihydroxy-6-Methylpyrimidine
5,6-Dihydro-2,4-Dihydroxypyrimidine
Dihydro-6-Methyluracil
Dihydrothymidine
Dihydrothymine
Dihydrouracil
Dihydrouridine
2,6-Dihydroxy-4-Amino-5-Nitrosopyrimidine
2,6-Dihydroxy-4-Aminopyrimidine
2,4-Dihydroxy-6-Methyl-5-Nitropyrimidine
2,4-Dihydroxy-6-Methylpyrimidine
2,4-Dihydroxy-5-Nitropyrimidine
4,6-Dihydroxy-5-Nitroso-2-Thiopyrimidine
4,6-Dihydroxypyrimidine
2,4-Dihydroxypyrimidine-6-Methylsulfone
2,4-Dihydroxy-2-Thiopyrimidine
1,5-Dimethylcytosine
N,N-Dimethyl-2'-Deoxycytidine
1,3-Dimethyluracil
5,6-Dioxyuracil
2,4-Dithiopyrimidine
3,N'-Ethenocytidine
5-Ethyl-2'-Deoxyuridine
2-Ethymercapto-4,6-Diaminopyrimidine
5-Fluoro-2'-Deoxyuridine
Hexobarbital
5-Hydroxymethyl Cytosine
5-Hydroxymethyl-2'-Deoxyuridine
4-Hydroxy-6-Methyl-2-Thiopyrimidine
5-Hydroxymethyluridine
4-Hydroxypyrazolo-(3,4-d)Pyrimidine
2-Hydroxypyrimidine
4-Hydroxypyrimidine
4-Hydroxy-2-Thiopyrimidine
5-Hydroxyuracil
5-Hydroxyuridine
6-Hydroxyuridine
5-Iodocytidine
5-Iodocytosine
5-Iodo-2'-Deoxycytidine
5-Iodoorotic Acid
5-Iodouracil
5-Iodouridine
2',3'-O-Isopropylidenecytidine
2',3'-Isopropylideneuridine 5'-Triphosphate
5-Mercaptouracil 2'-O-Methylcytidie
3'-O-Methylcytidine
5-Methylcytidine
5-Methylcytosine
5-Methyl-2'-Deoxycytidine
5-Methyl-2-Thiocytosine
4-Methyl-2-Thiouracil
2-O-Methylthymidine
3-Methylthymidine
4-O-Methylthymidine
1-Methyluracil
3-Methyluracil
6-Methyluracil
2',O-Methyluridine
3-Methyluridine
3'-O-Methyluridine
5-Methyluridine
5-Nitrobarbituric Acid
5-Nitro-6-Methyluracil
5-Nitroorotic Acid
5-Nitrosothiobarbituric Acid
5-Nitroso-2-4-6-Triaminopyrimidine
5-Nitrouracil
3'-Oxauracil
5-Propyl-2-Thiouracil
6-n-Propyl-2-Thiouracil
Ribavirin
5-Sulfaminouracil
2-Sulfanilamidopyrimidine
Tetrahydrouridine
2-Thio-6-Azauridine
2-Thio-5-Carboxyuracil
2-Thiocytidine
2-Thiocytosine
4-Thio-2'-Deoxyuridine
Thiomethyluracil
2-Thiopyrimidine
2-Thiouracil
5-Thiouracil
2-Thiouracil-5-Carboxylic Acid
4-Thiouridine
2,4,5-Triamino-6-Hydroxypyrimidine
4,5,6-Triamino-2-Hydroxypyrimidine
2,4,6-Triamino-5-Nitrosopyrimidine
2,4,6-Triaminopyrimidine
4,5,6-Triaminopyrimidine
2,4,6-Trichloropyrimidine
Trifluorothymidine
2,4,5-Trihydroxypyrimidine
Uramil Additionally, a substrate analog resistance mutation of the present invention can be introduced that increases a PdN accumulation through increased resistance to amino-acid analogs such as histidine analogs and tryptophan analogs, due to elevated levels of phosphoribosylpyrophosphate synthetase. Alternatively, arginine-analog resistance can be used to increase the amount or activity of carbamoyl phosphate synthetase, also increasing a PdN production. Resistance to the glutamine analog 6-diazo-5-oxonorleucine, which inhibits CTP synthetase (pyrG), can also result in increased PdN production.

Metabolic endproduct resistance mutations. Metabolic endproduct-resistance mutations can be introduced into PdN producing cells, according to the present invention, to enhance production of a PdN. An endproduct resistance-mutation can be introduced into a PdN producing microbial cell by exposing mutagenized or non-mutagenized cells to increasing concentrations of the endproduct in the medium, such that surviving cells possess a mutation imparting resistance to that endproduct. As mentioned previously, a plasmid containing one or more genes that confer endproduct resistance can also be employed to transform a PdN-producing cell, thereby increasing PdN production. Again plasmid and cellular sources for such mutations are for example, commercially available, from the *E. coli* Genetic Stock Center and the Bacillus Genetic Stock Center, among others.

A suitable endproduct resistance mutation would impart resistance, for example, to thiouracil, azauracil, fluorouracil, fluoroorotic acid, fluorocytidine, fluorodeoxyuridine, fluorodeoxycytidine, fluorouridine, azidothymidine, pyrimidine dideoxynucleotide, as well as other pyrimidine analogs such as the azidopyrimidines, cyanopyrimidines, and those presented in Table 1, above. These mutants provide increased PdN synthesis and accumulation, according to the present invention, by the fact that resistance to toxic analogs is often achieved by the overproduction of the PdN.

Additionally, a purine endproduct analog-resistance mutation can be introduced that affects the regulation of ribonucleotide reductase activity, or the activity of another pyrimidine biosynthetic enzyme, thereby to increase the production of a PdN by a recombinant microorganism. Examples of purine analogs are presented below in Table 2. A PdN endproduct-resistance mutation can thus be used, pursuant to the present invention, to produce more of a PdN than does a analogous, PdN-sensitive strain.

TABLE 2: PURINE ANALOGS

3'-O-Acetyl-2'-Deoxyadenosine
3'-O-Acetyl-2'-Deoxycytidine
N'-Acetyl-2'-Deoxycytidine
N'-Acetylguanine
2-Amino-6-Benzylmercaptopurine
2-Amino-6-Benzylthipurine
2-Amino-8-Bromo-6-Hydroxypurine
2-Amino-6(α-Carboxyethyl)-Mercaptopurine
2-Amino-6-Carboxymethyl-Mercaptopurine
2-Amino-6-Chloropurine
2-Amino-6-Chloropurine Riboside
6-Amino-2,8-Dihydroxypurine
8-Aminoguanosine
2-Amino-6-Mercaptopurine
6-Amino-2-Methylpurine
6-Amino-3-Methylpurine
2-Aminopurine
8-Azaxanthine
8-Azidoadenosine
6-Benzylaminopurine
6-Benzylaminopurine Riboside
1-Benzylinosine
8-Bromoadenine
8-Bromoadenosine
8-Bromo-2'-Deoxyguanosine
8-Bromoguanine
8-Bromoguanosine
8-Bromoinosine
6-Bromopurine
6-Carboxymethymercaptopurine
2-Chloroadenosine
5'-Chloro-5'-Deoxyadenosine
5'-Chloro-5'-Deoxyinosine
8-Chloro-2,6-Dihydroxypurine
6-Chloroguanine
6-Chloroguanine Riboside
6-Chloroguanosine
6-Chloropurine
6-Chloropurine Riboside
8-Chloroxanthine
Cordycepin
6-Cyanopurine
2,6-Dichloropurine
2'-3'-Dideoxyadenosine
2'-3'-Dideoxyguanosine
2,8-Dihydroxyadenine
2,6-Dihydroxy-1-Methylpurine
2,6-Dihydroxypurine
2,6-Dihydroxypurine
6-Dimethylaminopurine
6-Dimethylaminopurine-9-Riboside
1,1-Dimethylguanidine
1,7-Dimethylguanine
1,7-Dimethylguanosine
N'-Dimethylguanosine
1,7-Dimethylxanthine
3,7-Dimethylxanthine
2,8-Dithio-6-Oxypurine
2,6-Dithiopurine
1,N'-Ethenoadenosine
6-Ethoxypurine
9-Ethyladenine
5'-(N-ethyl)-Carboxamidoadenosine
9-Ethylguanine
6-Ethylmercaptopurine
6-n-Heptylmercaptopurine
6-n-Hexylaminopurine
6-Histaminopurine
N'-(2-Hydroxyethyl)Adenosine
6-(β-Hydroxyethylamino)Purine
1-Hydroxy-iso-Guanine
2-Hydroxy-6-Mercaptopurine
6-Hydroxy-2-Mercaptopurine
2-Hydroxy-6-Methylpurine
6-Hydroxy-1-Methylpurine
2-Hydroxypurine
6-Hydroxypurine
2-Hydroxy-6-Thiopurine
6-Hydroxy-2-Thiopurine
5'-Iodo-5'-Deoxyadenosine
6-Iodopurine
N'-(Δ'-Isopentenyl)Adenosine
6-Isopropoxypurine
2',3'-O-Isopropylideneadenosine
2',3'-O-Isopropylideneguanosine
2',3'-O-Isopropylideneinosine
2',3'-O-Isopropylidene-6-Thioinosine
2-Mercaptoinosine
2-Mercaptopurine
6-Mercaptopurine
6-Mercaptopurine Arabinoside
6-Mercaptopurine 2'-Deoxyriboside
6-Mercaptopurine Riboside
2-Mercaptopyrimidine
6-Methoxypurine
6-Methoxypurine Riboside
1-Methyladenine
2-Methyladenine
3-Methyladenine
1-Methyladenosine
2'-O-Methyladenosine 3'-O-Methyladenosine
6-Methylaminopurine
1-Methylguanine
7-Methylguanine
1-Methylguanosine
2'-O-Methylguanosine
3'-O-Methylguanosine
7-Methylguanosine
1-Methylhypoxanthine
1-Methylinosine
7-Methylinosine
Methylmercaptoguanine
6-Methylmercaptopurine
6-Methylmercaptopurine Riboside
6-Methylpurine
6-n-Propoxypurine
6-n-Propylmercaptopurine
6-Selenoguanosine
6-Selenoinosine
6-Selenopurine
6-Thioguanine
6-Thioguanosine
8-Thioguanosine
Thiohydroxypurine
2-Thioxanthine
6-Thioxanthine
2,6,8-Trichloro-7-Methylpurine
2,6,8-Trichloropurine
1,3,9-Trimethylxanthine
2,6,8-Trioxypurine Purine- pyrimidine- and nucleoside-transport mutations. Purine-, pyrimidine- or nucleoside-transport mutation can be introduced into a PdN-producing cell of the present invention by transduction from a characterized strain that carries a mutated gene encoding a nucleoside-transport protein. A suitable transport mutation can also be effected by direct mutation, such that the transport mutation increases a PdN concentration in the cell medium. In either case, increased PdN accumulation results from a decrease in the activity or concentration of nucleoside-transport proteins, For example, there are nucleoside uptake-receptor mutations like nupG and nupC (nucleoside uptake mutation) and tsx (phage T6 resistance and nucleoside transport mutation). Plasmid and cellular sources for such mutations are commercially available, for instance, from the university sources mentioned above. Examples of a cell having such transport mutations include $E.$ $coli$ strains CMG 1118 and CMG 1158 (see Example 9, below).

Mutations that affect metabolic enzyme activity. To achieve increased PdN production, metabolic mutation can also be introduced by transforming a PdN-producing cell of the present invention with a plasmid that confers increased or decreased enzyme activity. For example, a deo operon mutation can be introduced into a PdN-producing cell, such that the mutation inhibits the synthesis or activity of the enzyme thymidine phosphorylase (deoA), which catalyzes the degradation of thymidine (e.g., see strain CMG 1004 of Example 9). Additionally, a uridine phosphorylase (udp) mutation can be introduced that lowers the amount or activity of uridine phosphorylase, thereby decreasing the degradation of thymidine or deoxyuridine which is a substrate for uridine phosphorylase (e.g., see strains CMG 1096 and CMG 1105 of Example 9). Also, a phosphoglucose isomerase (pgi) mutant can be introduced that further increases PdN-production by shifting carbohydrate metabolism to the hexose monophosphate pathway, resulting in an increased level of ribose in the cell. In another embodiment of the present invention, a thymidine kinase-inhibiting mutation can be introduced that prevents the phosphorylation of thymidine to make TMP, thereby increasing the production of thymidine.

Alternatively, a thymidylate synthase mutation can be introduced that prevents the formation of TMP from dUMP, thereby increasing the accumulation of dUMP and deoxyuridine. An organism carrying such a mutation would need an active thymidine kinase enzyme to allow for the utilization of thymidine for growth. The inhibition of thymidylate synthase can be effected by the use of a temperature-sensitive enzyme or the regulated expression of a gene encoding a thymidylate synthase inhibitor obtained, e.g., from a hydroxymethyluracil-containing Bacillus bacteriophage, such as phages phiE, SP82G or SP8, using conventional procedures. See Haslam et al, $Biochem.$ $Biophys.$ $Acta$ 134:312 (1967); Hayward $Virology$ 38:538 (1969); Roscoe & Tucker, $Biochem.$ $Biophys.$ $Res.$ $Comm.$ 16:106 (1964); and Roscoe & Tucker, $Virology$ 29:157 (1966). The dUMP can then be converted to deoxyuridine by a PdNPase, such as dTMPase. Thus, deoxyuridine can specifically accumulate in the medium in recoverable amounts, produced by a PdN producing cell according to the present invention.

Other DNAs that encode other metabolic enzymes can also be introduced, pursuant to the present invention, to enhance the production of a PdN. Suitable DNAs in this context would include those that code for a carbamoyl phosphate synthase (carAB), an aspartate transcarbamoylase (pyrBI), a dihydroorotase (pyrC), a dihydroorote oxidase (pyrD), an orotate phosphoribosyltransferase (pyrE), an orotidine 5'-phosphate decarboxylase (pyrF), a CTP synthase (pyrG), a nucleoside-phosphate kinase (pyrH), a phosphoribosylpyrophosphate synthetase (prs), a nucleoside diphosphate kinase (ndk), a ribonucleoside diphosphate reductase (nrd), a dCTP deaminase (dcd), a dUTPase (dut), a thymidylate synthase (thyA), a serine hydroxymethyltransferase (glyA), a dihydrofolate reductase (folA), a thioredoxin (trxA), a thioredoxin reductase (trxB), a glutathione reductase, a glutathione synthase, a glutaredoxin, a dTTPase, a dCTPase and a dCMP deaminase. These genes are readily available from commercial sources, including those university-based collections mentioned above and the ATCC (Rockville, Md.). These genes can also be cloned via conventional procedures (see, e.g., Ausubel et al, eds. CURRENT PROTOCOLS IN MOLECULAR BIOLOGY, Wiley Interscience, New York, [1987, 1989]), based on a published DNA-sequence or genetic-mapping information.

Cultured cells that are suitable for expressing a PdN in recoverable amounts, according to the present invention, include cultured prokaryotic and eukaryotic cells that would express a recombinant DNA sequence encoding a PdNPase enzyme that allows for the accumulation of a PdN in recoverable amounts. In a preferred embodiment, conventional techniques (see generally Ausubel et al, supra) can be used to incorporate a cloned PdNPase-encoding DNA into cultured bacterial cells such as $B.$ $subtilis$ (see, e.g., Hardy, In DNA CLONING, IRL Press, Oxford 2:1-17 [1985]), $E.$ $coli$ or Corynebacterium (see, e.g., Dunican & Shivnan, $Biotechnology$ 7:1067–70 [1989]), and into eukaryotic cultured cells such as Saccharomyces, to produce a PdN in recoverable amounts. However, other cell types would also be suitable for producing a PdN according to the present invention, since the general metabolic pathway for the production of a PdN is similar in most types of cells.

*E. coli* and *B. subtilis* are preferably used in the present invention because the genetics of pyrimidine biosynthesis is well-understood, the techniques for strain construction by both classical genetic and recombinant DNA technology are well-developed, and the strains do not produce toxic byproducts such as endotoxins. In a preferred embodiment, as the parent strain, either a wild type *Bacillus subtilis* strain or, more preferably, a strain already carrying one or more of the mutations described above will be used.

The present invention is further described by the following illustrative examples.

EXAMPLE 1

Purification of a Representative Pyrimidine Deoxyribonucleotide Phosphohydrolase (PdNPase)

For production and purification of the PdNPase, dTMPase, *B. subtilis* CMG356 (ATCC 33234) was grown at 37° C. to an $OD_{600}$ of 1.0 and bacteriophage PBS1 was added at a multiplicity of infection of approximately 2.5–5. After 30 minutes incubation with shaking, the culture was chilled on ice and the cells were harvested by centrifugation. The cells were resuspended in buffer A (10mM Tris-HCl, pH 7.5, containing 1 m M ethylenediaminetetraacetic acid [EDTA]) and broken by passage one time through a French pressure cell. The cellular debris was removed by centrifugation, and nucleic acids were precipitated from the extracts by addition of streptomycin sulfate to a final concentration of 1.15% (w/v). The precipitated nucleic acids were removed by centrifugation and the streptomycin supernatant solution was used for purification of the enzyme.

Ammonium sulfate was added to the streptomycin sulfate supernatant to give a final concentration of 50% (w/v). The precipitated proteins were removed by centrifugation and the supernatant solution was applied to a column (2.6×20 cm) of Phenyl-Sepharose TM (Pharmacia LKB) that was equilibrated with 50% ammonium sulfate in Buffer A. The column was washed with approximately 100 ml of Buffer A+0.1M NaCl, and the enzyme was eluted from the column with a linear gradient of buffer made from 200 ml of Buffer A+0.1M NaCl and 200 ml of Buffer A, followed by 200 ml of distilled water. The fractions were then assayed for dTMPase activity.

The assay for dTMPase was carried out as follows. The assay mix was prepared as 10 μl 1M MES at pH 6.2; 5 μl of 100 mM $MgCl_2$; 5 μl 10 mM EDTA; 15 μl of 20 mM dTMP; and $H_2O$ to a final volume of 125 μl including enzyme. The assay mix was placed in a microfuge tube, a fraction containing the enzyme was added and incubated at 37° C. for 15 min. Next, 200 μl of acid molybdate reagent (Sigma) was added, followed by 925 μl of Fiske-Subbarow reducer (8.6 mg/ml in water, freshly prepared). This mixture was left at room temp for 20 min, and then the absorbance at 750 nm ($A_{750}$) was read. The inorganic Pi was calculated based on a standard curve.

The fractions containing dTMPase activity were pooled and loaded directly onto a column (1.6×20 cm) of DEAE-ion exchange column (a suitable column is a Sephacel TM column, available from Pharmacia-LKB) equilibrated with Buffer A. The column was washed with 50 ml of Buffer A+0.1M NaCl, and the enzyme was eluted with a linear gradient made from 200 ml of Buffer A+0.1M NaCl and 200 ml of Buffer A+0.3M NaCl. The enzyme was eluted at a NaCl concentration of about 0.2–0.25M.

The active fractions from the DEAE-Sephacel TM column were pooled and concentrated by diluting the solution 1:1 with Buffer A, binding the enzyme to a small (2 ml) column of DEAE Sephacel TM, and eluting it in a minimal volume of Buffer A with 0.5M NaCl. The concentrated enzyme preparation was loaded onto a column of Sephadex TM G-100 (1.6×100 cm) equilibrated with Buffer A and eluted with the same buffer. The active fractions were concentrated on a small DEAE column as above and dialyzed against Buffer A. From 20 g (wet weight) of cells, approximately 2 mg of enzyme were isolated. The purified enzyme was analyzed by SDS polyacrylamide gel electrophoresis and was determined to have a molecular weight of approximately 29,000 daltons, with a purity of at least 90%. Approximately 100 μg of the enzyme preparation were used for the determination of the amino-terminal (N-terminal) sequence of the protein.

EXAMPLE 2

Protein Sequencing of a Purified PdNPase (dTMPase)

The purified dTMPase protein preparation obtained in Example 1 was used for amino-terminal sequencing by conventional techniques (see, e.g., Needleman, PROTEIN SEQUENCE DETERMINATION, Springer-Verlag, N.Y. (1970)). The sequence of the first twenty amino acids at the amino terminus of dTMPase and the possible nucleotide sequences coding for the enzyme are presented in FIG. 3.

Based on the different nucleotide sequences that can be inferred from the amino acid sequence, two sets of mixed oligonucleotide probes were obtained from commercial sources. The sequences of the probe mixtures and the corresponding amino acid sequence are presented in FIG. 4. All possible combinations of codons that may code for the first seven amino acids were included in the 20-base oligonucleotide probes.

Figure 5:
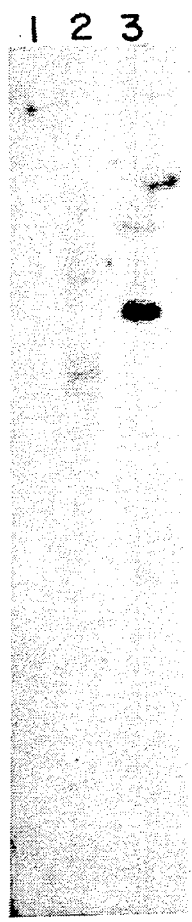
FIG. 5 is a depiction of an autoradiogram of the hybridization of oligonucleotide probes to E. coli-, B. subtilis- and and PBS 1-DNA fragments (lanes 1, 2 and 3, respectively) on a nitrocellulose filter.

Both mixtures of oligonucleotide probes were end-labeled with $^{32}P$ and used to hybridize against a Southern blot of EcoRI restriction endonuclease digests of bacteriophage PBS DNA and of *B. subtilis* and *E. coli* genomic DNA. End-labeling, hybridizations, Southern blots, and similar experiments were performed according to, generally, Maniatis et al, MOLECULAR CLONING: A LABORATORY MANUAL, Cold Spring Harbor Laboratory, New York, (1982). Under low stringency conditions, a 5-kb EcoRI fragment from PBS1 hybridized strongly (FIG. 5) to the probes while several lighter bands were observed in the *B. subtilis* genomic DNA lane. No detectable hybridization to *E. coli* genomic DNA, however, was observed. The low stringency hybridization (27° C.) and wash (38° C.) conditions necessary to obtain a strong signal for the PBS1 dTMPase DNA were lower than expected, based on the melting temperatures ($T_m$'s) calculated for the oligonucleotides.

EXAMPLE 3

Representative PdNPase (dTMPASE) DNA Isolation

Bacteriophage PBS1 DNA was isolated from phage particles for the preparation of a DNA library. A PBS1 phage lysate (1000 ml, approx. $5 \times 10^8$ pfu/ml), was treated with deoxyribonuclease I (1 mg/L) and ribonuclease A (1 mg/L) to eliminate host nucleic acids. After nuclease digestion, the lysate was passed through a 0.45 micron filter to remove cellular debris and any cells that were not lysed by infection with PBS1. Phage particles were then precipitated by the addition of NaCl to 0.5M and polyethylene glycol 8000 to a concentration of 6% (w/v), and collected by centrifugation. Contaminating host nucleic acids and cellular debris were further eliminated by pelleting the phage through a 5-40% glycerol block gradient made in 0.1M sodium phosphate, pH 7.0, 0.1M NaCl (phosphate buffer). The phage particles were suspended in phosphate buffer, and DNA was isolated by treatment with 2% SDS followed by extraction several times with phenol and with n-butanol, followed by dialysis against 0.01M Tris-HCl, 0.001M EDTA, pH 8.0. From one liter of lysate, approximately 8.6 mg of high molecular weight DNA were obtained.

EXAMPLE 4

Generation of DNA Library Containing DNA Encoding A PdNPase (dTMPASE)

To generate a DNA library with a random representation of the PBS1 genome (see, e.g., Maniatis, supra), PBS1 DNA was partially digested with DNaseI to cleave the DNA randomly into fragments that were in the one to five kilobase pair (kb) range. The DNA was then treated with T4 DNA polymerase to ensure that the ends were flush, and the fragments were size fractionated by gel electrophoresis to obtain fragments in the range of 1-5 kb. Subsequent blunt-end ligation of the fragments with SmaI-linearized plasmid pUC19 and transformation of E. coli strain KT8052 (Kunkel et al, Methods in Enzymol. 154:367-82 [1987]) yielded recombinant transformants at a frequency of approximately 7%. The average insert size (estimated from the sum of BamHI and EcoRI double digestion fragments) was found to be at least 2 kb. This average insert size was large enough to contain the dTMPase gene (estimated coding sequence of about 900 bp) along with the flanking regulatory sequences.

EXAMPLE 5

Screening the DNA Clone Library for PdNPase (dTMPASE) Encoding DNA

Figure 6:
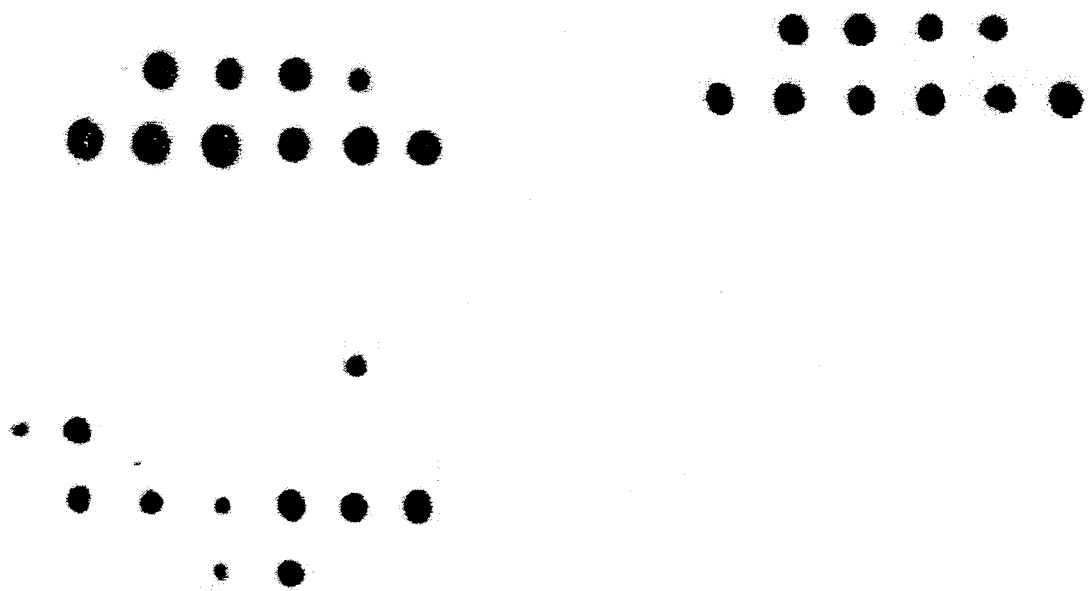
FIG. 6 is a picture of an autoradiogram depicting colony hybridization of putative clones of dTMPase-encoding DNA.

The gene library of DNaseI-generated PBS1 DNA fragments in pUC19 was screened using conventional techniques (see, e.g., Maniatis, supra) by colony hybridization with the oligonucleotide probes that were radioactively-labelled with $^{32}P$ by using polynucleotide kinase and a few strong positive clones were identified above a relatively high background. The putative positive clones were picked and plated at low colony density onto LB+ampicillin plates containing the lac inducer IPTG and X-gal indicator. Several white colonies (recombinant clones) from each plate were picked onto LB+ampicillin plates and transferred to nitrocellulose filters after growth and plasmid amplification by exposure to chloramphenicol. The colonies were re-screened by hybridization with the oligonucleotide probes and some of the positive colonies in the re-screen are shown in FIG. 6. Colonies that hybridized strongly were further screened by Southern blot analysis of EcoRI-digested plasmid DNA. Two clones (pCG100 and pCG101) that contained the 5'-end of the dTMPase gene were identified and verified by DNA sequence analysis to encode for dTMPase. Both clones were missing the sequence at their respective 3'ends, as indicated by the length of the coding region of each clone.

Figures 8, 9:
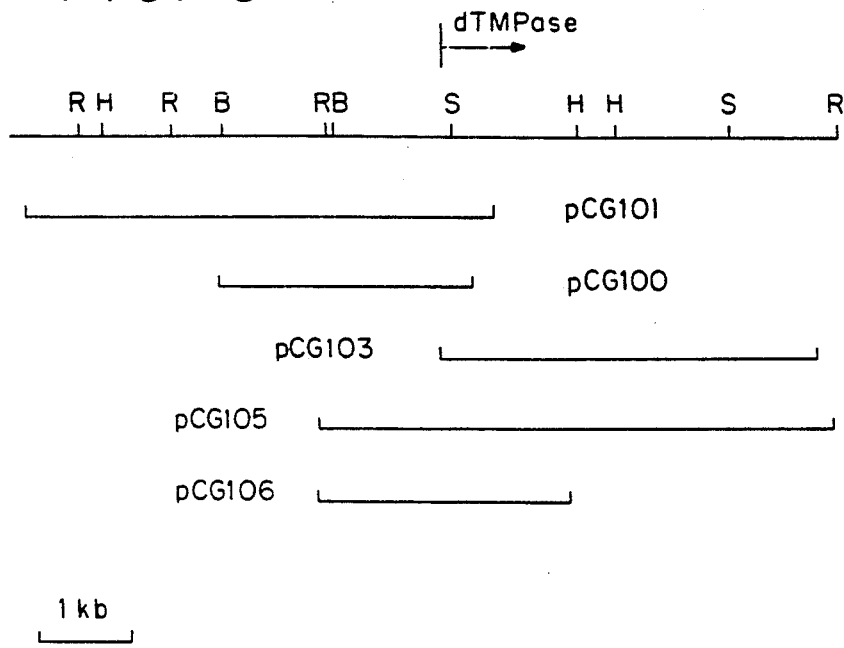
FIG. 8 is a diagrammatic representation of partial and complete exemplary clones of a dTMPase gene. Restriction endonuclease cleavage sites are denoted as R (EcoRI), B (BamHI), H (HindIII), and S (ScaI).
FIG. 9 is a representative oligonucleotide used for site-directed mutagenesis of plasmid pCG100.

Twenty-two additional putative positive clones were obtained by screening of the DNaseI-generated PBS1 DNA library with a $^{32}P$-labeled dTMPase-specific oligonucleotide probe. The probe in this case was a 17-base oligonucleotide complementary to bases 212-196 of the dTMPase gene shown in FIG. 7 (as subsequently sequenced by conventional techniques after isolation of the entire coding sequence). After re-screening, ten positive clones containing dTMPase gene sequences were identified. Characterization of these ten positive clones by restriction analysis produced one clone (pCG103) with a PBS1 DNA insert large enough (4.5 kb) to contain the entire dTMPase gene. The remaining nine clones were similar to clones 19 (pCG100) and 20 (pCG101). They contained sequences from the 5'-end of the dTMPase gene and terminated before what was predicted to be the 3'-end of the gene. The exact upstream boundary for the dTMPase gene sequence present in plasmid pCG103 was determined by DNA sequence analysis and was found to be located at nucleotide 88 of the dTMPase gene. Although pCG103 did not contain the entire dTMPase gene, it missed only 88 nucleotides present on overlapping fragments from pCG100 and pCG101 (FIG. 8). These overlapping fragments were combined to regenerate the entire dTMPase gene on a single fragment.

EXAMPLE 6

Cloning of a Representative PdNPase (dTMPASE) Gene into E. coli

In order to reconstruct the gene for dTMPase to allow for expression of the desired enzyme activity, overlapping fragments of two of the partial clones were recombined in such a way as to create a complete gene coding for dTMPase. The two clones used were pCG100 and pCG103 (FIG. 8). The sequence of the portion of dTMPase located in plasmid pCG100 was subcloned into bacteriophage M13 and modified by site-directed mutagenesis using oligonucleotide AY006 (FIG. 9) to place an EcoRI site between the predicted promoter of the gene and the ribosome binding site as shown (FIG. 10).

Figure 10:
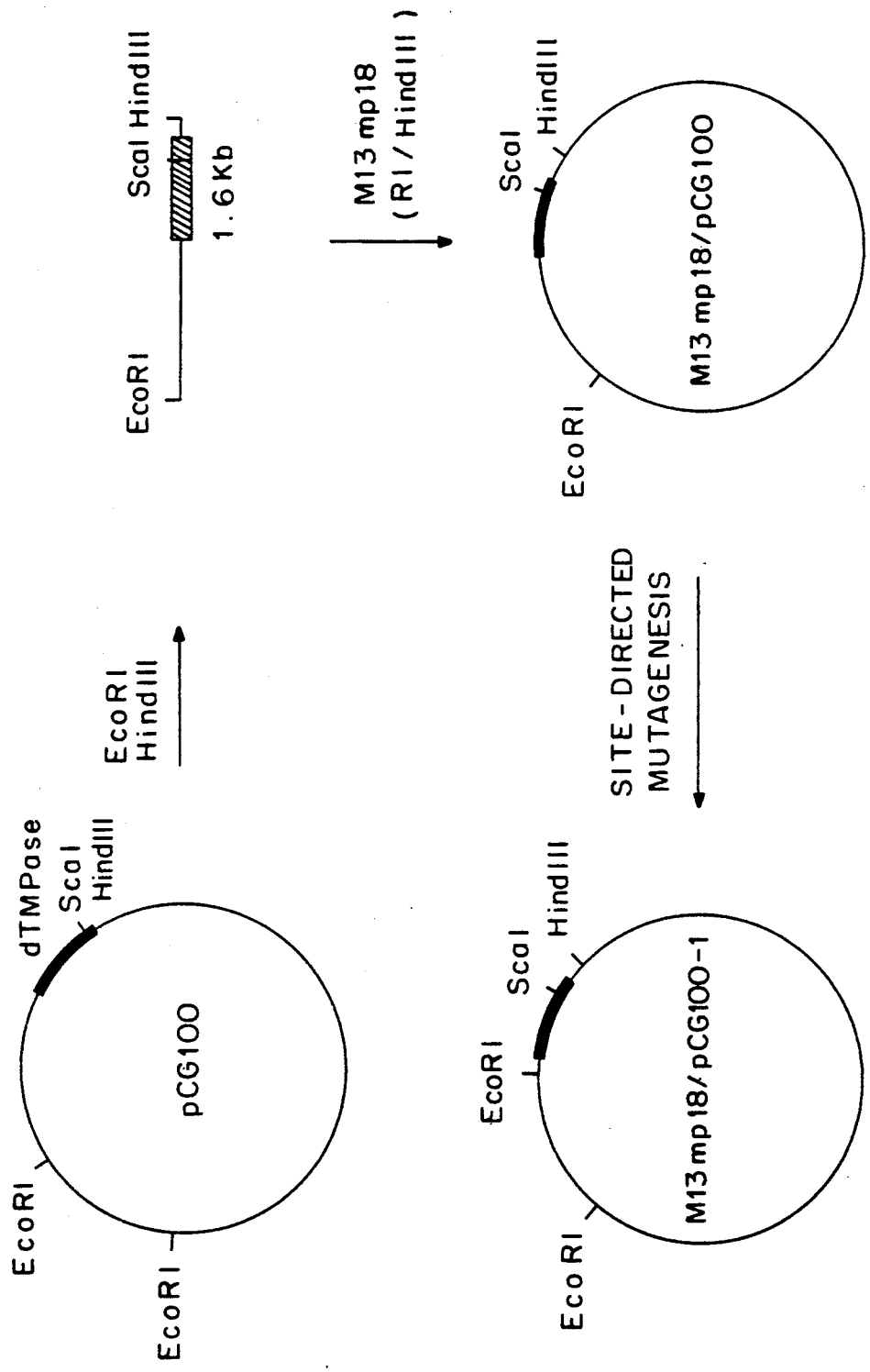
FIG. 10 is flow chart representing an exemplary site-directed mutagenesis of a dTMPase fragment of pCG100.
Figure 11:
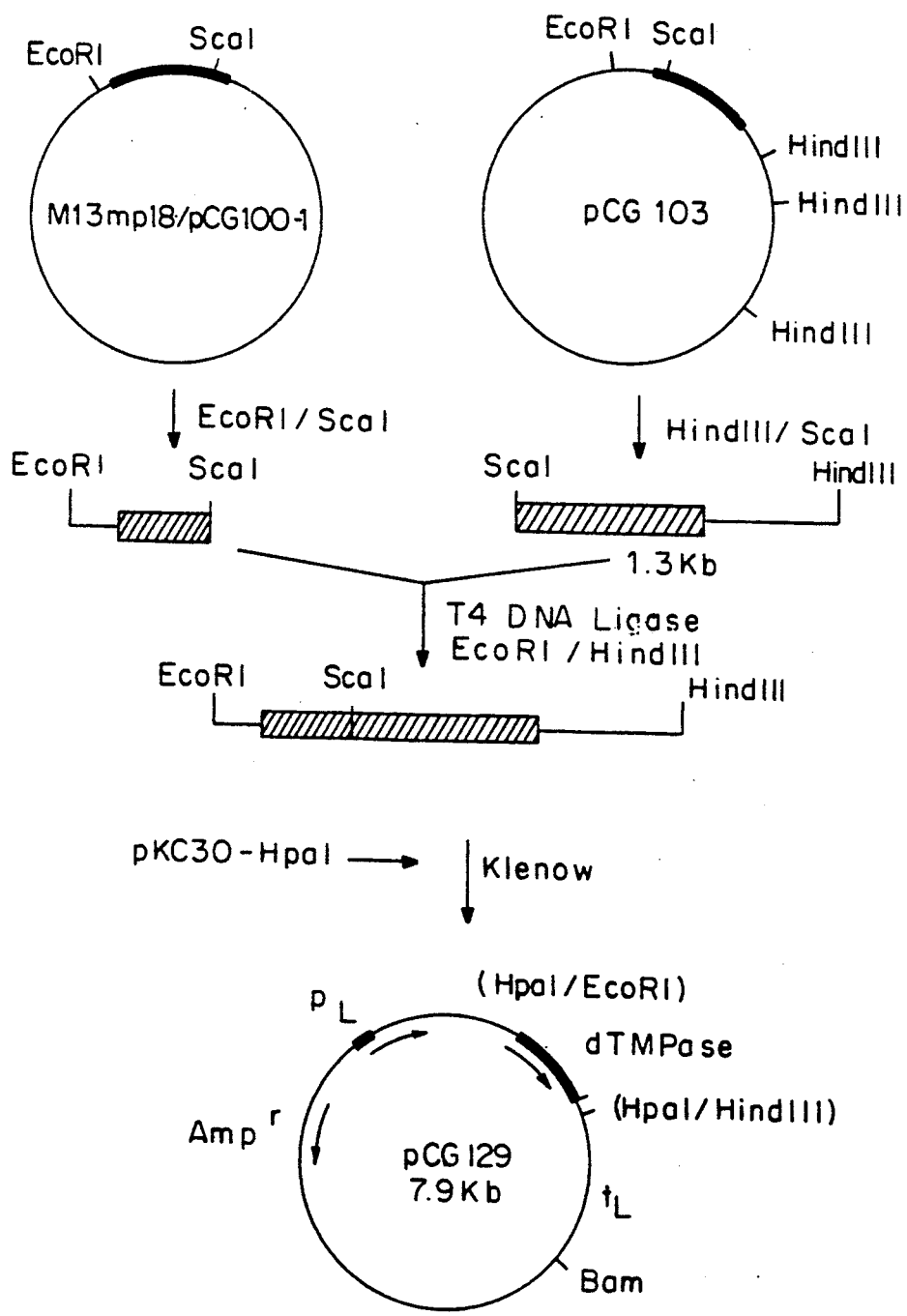
FIG. 11 is a diagram depicting a reconstruction of a representative dTMPase gene from clones pCG100 and pCG103, both cloned into vector pKC30.

As also shown in FIG. 10, from the mutagenized M13 RF DNA, a 196 bp EcoRI-ScaI fragment carrying the dTMPase ribosome binding site and bases 1 to 176 of the coding sequence was obtained. From pCG103, as shown in FIG. 11, a 1300 bp ScaI-HindIII fragment containing the remainder of the dTMPase coding region an about 750 base pairs at the 3'-end of the gene was obtained. The two fragments were ligated at the ScaI sites to create a DNA fragment consisting of the entire coding region for dTMPase. After filling in the EcoRI and HindIII ends with DNA polymerase (Klenow), the fragment was blunt-end ligated into the HpaI site of plasmid pKC30 downstream from the lambda $p_L$ promoter (FIG. 11). The plasmids were transformed into E. coli K-12 ΔH1 (ATCC 33767), which has the temperature-sensitive lambda cI857 repressor on the chromosome. At 30° C., the repressor was active and keeps $p_L$ turned off. At 42° C., the cI857 repressor was inactivated, resulting in high level expression from $p_L$. Of the transformants in E. coli ΔH1, one had a plasmid (pCG129) that has the predicted restriction map and it was analyzed further. *E. coli* ΔH1 carrying pCG129 has been named CMG1085.

EXAMPLE 7

Expression of dTMPASE in *E. coli*

Strain CMG1085 was grown to an $OD_{600}$ of about 1.0 in LB broth containing 0.1 g/L of ampicillin, the culture was shifted to 42° C. for 15 minutes and back to 37° C. for 45 minutes. 1 ml of culture was spun down in an 1.5 ml centrifuge tube, and the supernatant removed. Cells were then washed once with saline or water and re-spun. The cell pellet was then freeze-thawed and resuspended in 100 μl of TE (10 mM Tris-HCl, pH 7.5, 1 mM EDTA). 1 μl of lysozyme (5 mg/ml in TE) was added and incubated for 20 minutes at room temperature. 100 μl of DNase I mixture (2 ug/ml DNase I in TE+10 mM $MgCl_2$) was added and incubated for 10 minutes at room temperature. The solution was then spun for 10' at 20,000 rpm. The supernatant was then assayed for dTMPase activity as in EXAMPLE 1.

The results of the assay are shown in Table 3.

TABLE 3 dTMPase activity of crude extracts

| Strain | Specific activity (μmol/min/mg) |
| --- | --- |
| *E. coli* ATCC33876 with pUC19 | 0.019 |
| *E. coli* CMG1085 | 1.120 |
| *B. subtilis* CMG356 infected with bacteriophage PBS1. | 0.114 |

The enzyme-containing extracts were also analyzed by Western blot analysis and it was seen that at 30° C., there was no cross-reacting material present, while in de-repressed cells, there was a large amount of enzyme made and the enzyme co-migrated with purified dTMPase from bacteriophage PBS1. These results demonstrated that the dTMPase gene of bacteriophage PBS1 was cloned and expressed. The coding region described above codes for dTMPase, and its molecular weight as determined by SDS-PAGE was about 29,000, which corresponds to the value obtained for the purified dTMPase isolated from PBS1-infected *B. subtilis*. After temperature induction, the cultures were plated to test for viability and were found to have decreased viability as soon as any enzyme activity was present.

Figure 12:
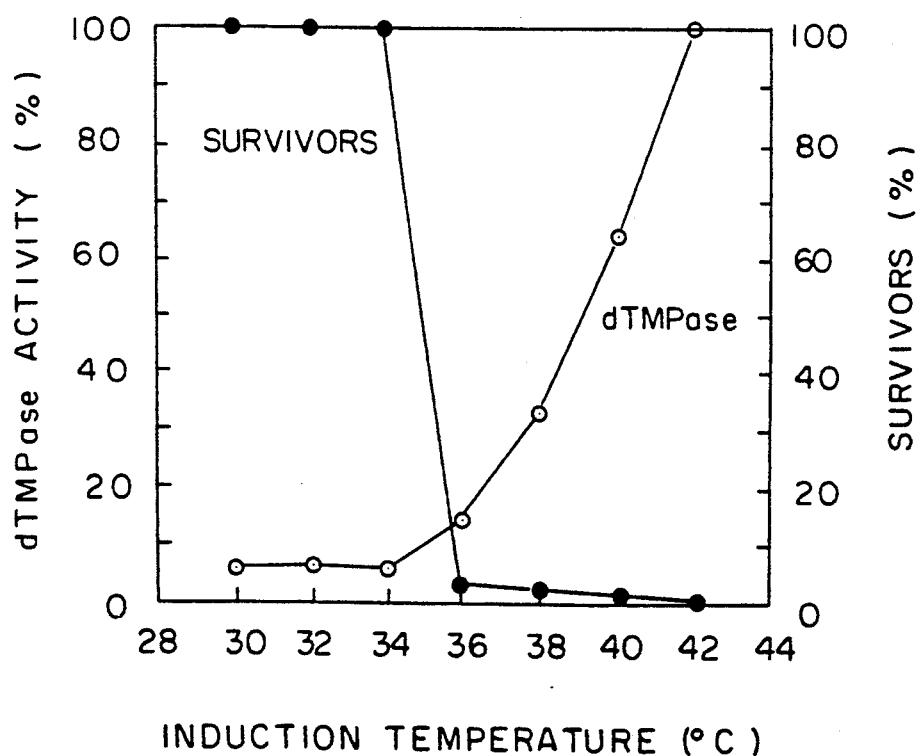
FIG. 12 is a graph depicting the dependence of dTMPase activity on induction temperature compared to cell viability.

To further examine the effect of induction temperature on enzyme activity and viability, cultures were grown at 30° C. to an $OD_{600}$ of about 1.0 and then shifted to several higher temperatures. After 90 minutes at the elevated temperature, the cells were harvested and extracts were made and assayed. At the same time, the cultures were plated to test for viability. The results are shown in FIG. 12. The figure shows that viability and enzyme activity were closely related and that a little activity can lead to a large decrease in viability.

EXAMPLE 8

Integration of the dTMPASE Gene into the Chromosone

Figure 13:
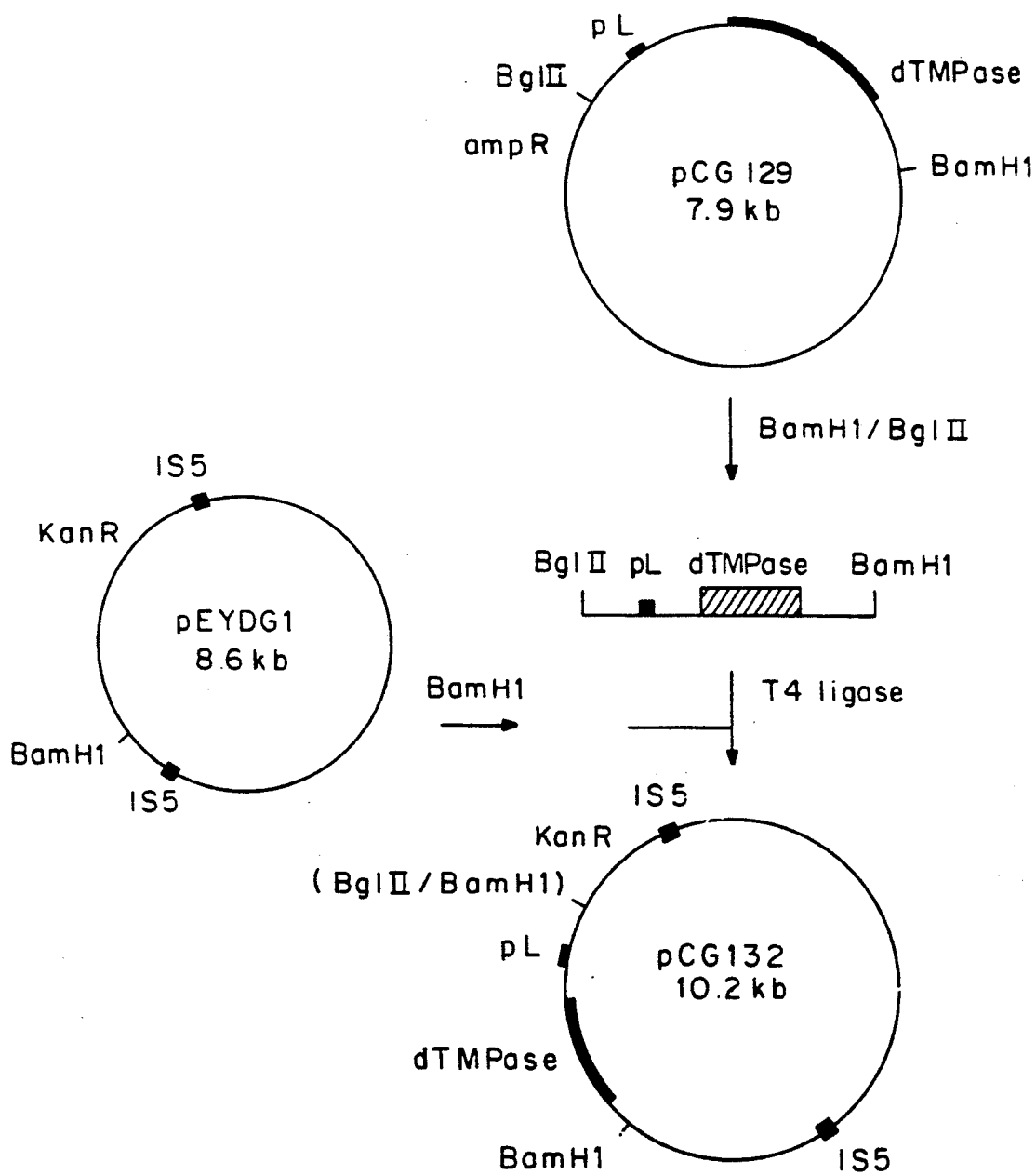
FIG. 13 is a diagram depicting the construction of pCG132, with dTMPase inserted into transposon Tn5 in plasmid pEYDG1.

In order to have a strain that produced less dTMPase activity and did not have the gene on a plasmid, the dTMPase gene was integrated into the *E. coli* chromosome. In order to integrate the dTMPase/lambda $p_L$ regulon into the chromosome, a fragment from plasmid pCG129 carrying the gene and the promoter was cloned into transposon Tn5 (Tn5) (see Yakobson and Guiney, *J. Bacteriol.* 160:451-453 (1989)) carried on plasmid pEYDG1 (deposited as ATCC 37316) as shown in FIG. 13, to give the plasmid pCG132. The plasmid was then introduced into strain CMG1096. Very few transformants were obtained, and those that were had no detectable plasmids. Cells carrying plasmids, and thus having a high number of copies of the dTMPase gene, were selected against, and only strains in which the gene had become integrated by transposition of the Tn5-dTMPase were obtained.

The gene was integrated with the kanamycin resistance gene on Tn5, so that it can now be easily moved to different strains by P1 transduction. The dTMPase gene activities of chromosome integrated dTMPase strains compared with those of the plasmid containing strains where found to have approximately a five-fold less activity.

EXAMPLE 9

*E. coli* Strains Constructed

Figure 14:
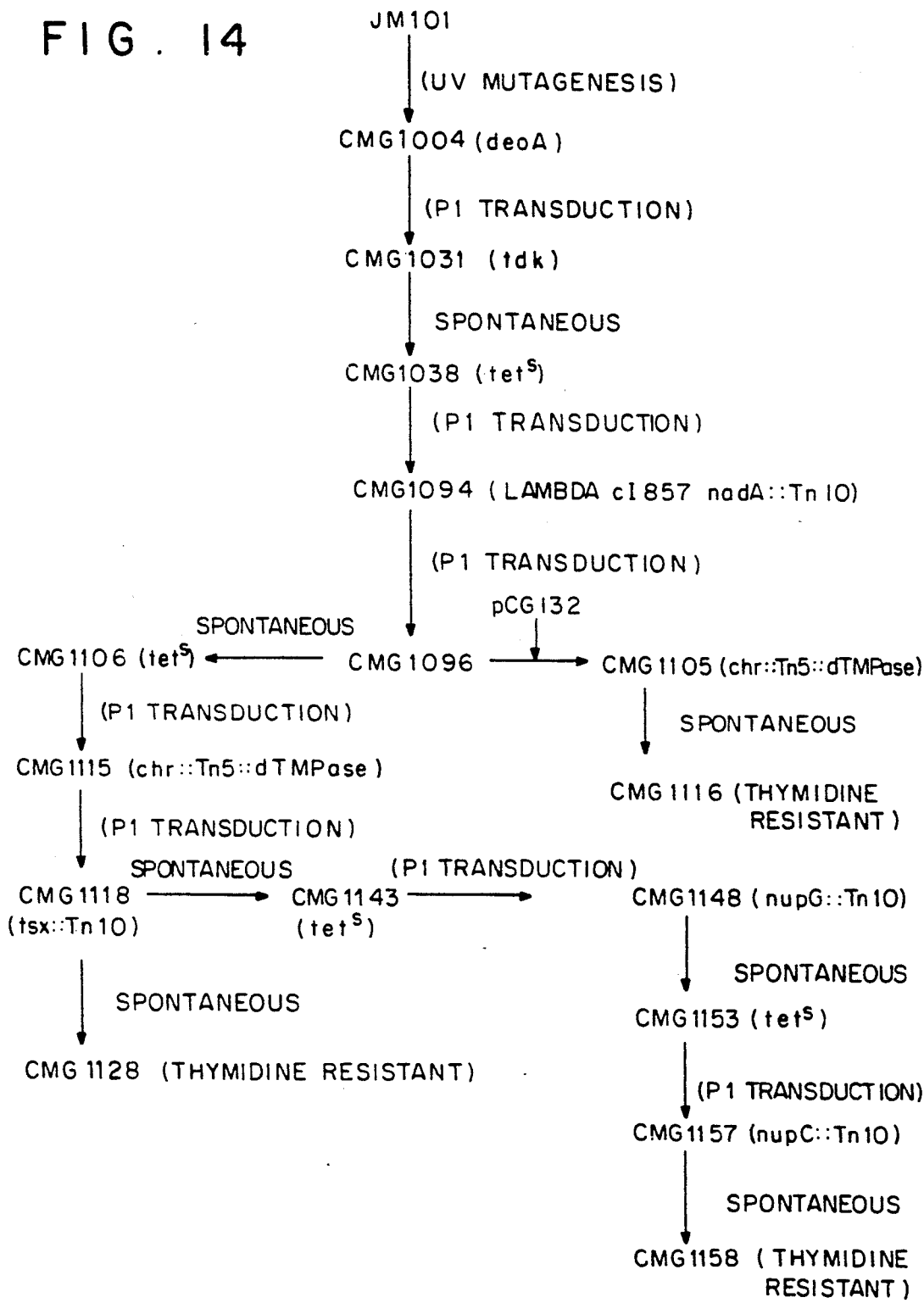
FIG. 14 is a flow chart depicting the lineage of some representative genetically modified E. coli strains.

All *E. coli* strains containing the chromosomal dTMPase gene carry the temperature sensitive lambda cI857 repressor in a defective lambda lysogen in the chromosome to allow for control of the dTMPase gene from the lambda $p_L$ promoter (Bernard et al, Gene 5:59–76 [1979]). Different strains were constructed by introducing mutations that either eliminated a PdN utilization, decreased a PdN accumulation inside the cell, deregulated the pyrimidine pathway, or decreased a PdN sensitivity. In most cases, the mutations were introduced by using a Tn10 insertion mutant, or co-transduction of a closely-linked Tn10 insertion, by selection for tetracycline resistance. From these strains, tetracycline sensitive derivatives with spontaneous Tn10 deletions were then selected so that other markers could be introduced in the same manner. Some representative strains that have been constructed are listed in Table 4, and the route of their construction is shown in FIG. 14.

PdN resistant mutants were obtained by growing in the presence of inhibitory levels of a PdN and were resistant to, e.g., 20 g/L of thymidine in the medium. All strains containing the dTMPase gene under control of lambda $p_L$ were temperature sensitive at 42° C. on LB plates.

TABLE 4

*E. coli* strains*

| Strain | Genotype |
| --- | --- |
| JM101 | supE, thi-1, Δ(lac-proAB), hsdR<sup>−</sup>M<sup>+</sup> (F' traD36, proAB, lacI<sup>q</sup>ZΔ M15) |
| CMG1004 | JM101 deoA |
| CMG1031 | CMG1004 tdk |
| CMG1038 | CMG1031 tet<sup>s</sup> |
| CMG1094 | CMG1038 chr::lambda cI857 nadA::Tn10 |
| CMG1096 | CMG1094 udp |
| CMG1106 | CMG1096 tet<sup>s</sup> |
| CMG1105 | CMG1096 chr::Tn5-dTMPase |
| CMG1115 | CMG1106 chr::Tn5::dTMPase |
| CMG1118 | CMG1115 tsx::Tn10 |
| CMG1128 | CMG1118 TdR<sup>r</sup> |
| CMG1158 | CMG1118 nupC::Tn10, nupG, TdR<sup>r</sup> |

*Key to abbreviations in Table 4:

| Symbol | Phenotype or enzyme encoded |
| --- | --- |
| supE | amber (UAG) suppressor |
| thi-1 | thiamine thiazole requirement |
| Δlac-proAB | deletion resulting in requirement for proline |
| hsdR<sup>−</sup>M<sup>+</sup> | host restriction-modification system |

TABLE 4-continued

| Strain | E. coli strains* Genotype |
|---|---|
| traD | F-factor transfer function |
| lacI<sup>q</sup> | high-affinity binding lactose operon repressor |
| deoA | thymidine phosphorylase |
| tdk | thymidine kinase |
| tet | tetracycline resistance |
| ung | uracil-DNA glycosylase |
| nadA | nicotinic acid requirement |
| udp | uridine phosphorylase |
| argR | repressor of arginine biosynthesis |
| tsx | phage T6 resistance, nucleoside transport mutation |
| TdR$^r$ | resistance to thymidine |
| nupC | nucleoside uptake mutation |
| nupG | nucleoside uptake mutation |
| trpE | anthranilate synthase, requirement for tryptophan |
| chr | integrated into the chromosome |

Some representative biosynthetic enzymes were cloned into expression plasmids so that they could be introduced into a thymidine producing cell of the present invention. Cloning was based on the published sequence (e.g., for thymidylate synthase and ribonucleotide reductase) and the plasmids carrying those genes are listed in Table 5.

TABLE 5

| Plasmid | List of Plasmids Description |
|---|---|
| pCG129 | pKC30 with cloned dTMPase controlled by lambda $p_L$ |
| pCG138 | pUC18 with thymidylate synthase controlled by lac promoter |
| pCG144 | pUC18 with ribonucleotide reductase controlled by the lac promotor. |
| pCG148 | pCG138 with ribonucleotide reductase gene downstream from thymidylate synthase, coordinately expressed |

EXAMPLE 10

Production of PdNS Using Engineered Strains

New strains were made as shown in FIG. 14 and listed in Table 4, and they were tested in shake flask experiments to compare PdN (as thymidine) production achievable relative to other strains available. Shake flask experiments were performed as follows. Cells were inoculated into 25 ml (in a 250-ml baffle flask) of the medium composition presented in Table 6.

TABLE 6

| Shake-Flask Medium (final concentration: g/L) | |
|---|---|
| K$_2$HPO$_4$ | 7 |
| NaH$_2$PO$_4$.H$_2$O | 3 |
| NH$_4$Cl | 1 |
| (NH$_4$)$_2$SO$_4$ | 5 |
| MgSO$_4$.7H$_2$O | 3 |
| carbon source | 2 |
| tryptone | 20 |
| proline | 2 |
| nicotinic acid | 0.2 |
| thiamine HCl | 0.2 |
| folic acid | 0.025 |
| p-aminobenzoate | 0.025 |
| kanamycin | 0.01 |
| tetracycline | 0.0125 |

The cells were grown to log-phase at 30° C. and 250 r.p.m. When the cultures reached an OD$_{600}$ of 0.5–1.0, uridine or uracil was added and the temperature was shifted to 36°–37° C. to induce the expression of dTMPase. Samples were taken at several time points and thymidine and other nucleosides were measured by HPLC, as described by Miller et al, J. Chromatog. 228:165–76 (1982). The titers ranged from 0–0.1 g/L thymidine at low cell density. In these experiments, glycerol was determined to be a better carbon source than glucose for thymidine production, uridine or uracil feeding at the time of dTMPase induction gave about equal productivity, and strains that were resistant to thymidine, including CMG1128 and CMG1158, gave the best titers consistently. All of the strains tested carried the gene for dTMPase on their chromosomes.

EXAMPLE 11

Production of PdNS in Shake Flasks at High Cell Density

Cultures of CMG1128 (containing pCG138), CMG1128 (containing pCG144), CMG1158 (containing pCG144) and CMG1158 (containing pCG148) were streaked on LB agar plates with 100 ug/mL ampicillin and grown at 30° C. Single colonies were picked into 25 mL of LB broth with 100 μg/ml ampicillin in a 250 mL baffle flask and incubated at 30° C. for 8 hours. This culture (0.5 mL) was used to seed flasks with thymidine production media with the composition presented in Table 7.

TABLE 7

| Thymidine-Production Medium | |
|---|---|
| K$_2$HPO$_4$ | 3.5 g/L |
| KH$_2$PO$_4$ | 1.5 g/L |
| (NH$_4$)$_2$SO$_4$ | 2.0 g/L |
| MgSO$_4$ | 0.4 g/L |
| sodium citrate | 0.5 g/L |
| calcium carbonate | 10 g/L |
| PP90BT (Deltown) | 8 g/L |
| glycerol | 50 g/L |
| biotin | 0.2 mg/L |
| thiamine | 1.0 mg/L |
| nicotinic acid | 1.0 mg/L |
| p-aminobenzoate | 1.0 mg/L |
| ampicillin | 0.1 g/L |
| ZnSO$_4$.7H$_2$O | 0.232 mg/L |
| MnSO$_4$ | 0.178 mg/L |
| H$_3$BO$_3$ | 0.056 mg/L |
| CuSO$_4$.5H$_2$O | 0.100 mg/L |
| Na$_2$MoO$_4$ | 0.039 mg/L |
| CoCl$_2$.7H$_2$O | 0.042 mg/L |
| KI | 0.066 mg/L |
| FeSO$_4$.7H$_2$O | 0.040 mg/L |
| NiCl.6H$_2$O | 0.0004 mg/L |
| phenol red | 0.1 g/L |

The 250 ml baffle flasks contained 25 ml of production medium and were incubated at 30° C. at 400 RPM in a NBS G25 shaker. When the cultures reached an optical density at 600 nm of 10 (read after dilution 1:11 into dilute sulfuric acid, 2 mL concentrated H$_2$SO$_4$ per 100 mL [to dissolve the CaCO$_3$ in the media]), the flasks were shifted from the 30° C. shaker to a 37° C. shaker at the same RPM. At that time the media was also supplemented with 1.14 g/L D,L-methionine, 2.86 g/L glycine, 14.3 g/L autolyzed yeast (Ardamine YEP-S, Champlain Industries), uracil 2.8 g/L, and 0.25 mM IPTG. The pH in the flasks was maintained at approximately 7.0 through the addition of 4N NH$_4$OH as judged by the color of the phenol red indicator dye.

Thymidine and deoxyuridine concentrations were measured by HPLC as described in Example 10. The product concentrations at 30 to 35 hours after inoculation were as presented in Table 8.

TABLE 8

| Strain | Product Concentrations | | OD$_{600}$ (max.) |
| --- | --- | --- | --- |
| | UdR (mg/L) | TdR (mg/L) | |
| CMG1128 (pCG138) | 64.9 | 385 | 20.3 |
| CMG1128 (pCG144) | 406 | 220 | 17.3 |
| CMG1158 (pCG144) | 416 | 269 | 21.5 |
| CMG1158 (pCG148) | 42.0 | 460 | 16.9 |

EXAMPLE 12

Alternative Ten Liter Productions of a PdN in a 14 Liter Fermentor

To exemplify a ten liter production of PdN such as thymidine, strain CMG1128-pCG138 was grown as above, but in a 14 liter fermentor, with the medium composition presented in Table 9.

TABLE 9

| Medium composition (final concentration: g/L) | |
| --- | --- |
| K$_2$HPO$_4$ | 7 |
| NaH$_2$PO$_4$.H$_2$O | 3 |
| NH$_4$Cl | 10 |
| (NH$_4$)$_2$SO$_4$ | 5 |
| MgSO$_4$.7H$_2$O | 3 |
| glycerol | 125 |
| tryptone | 20 |
| proline | 2 |
| nicotinic acid | 0.2 |
| thiamine HCl | 0.2 |
| folic acid | 0.025 |
| p-aminobenzoate | 0.025 |
| yeast extract | 10 |

When the OD$_{600}$ reached 10, the culture was fed the following nutrients to give the indicated final concentrations (in g/L) for uracil, 3; glycine, 1; methionine, 0.2; and serine, 1. The temperature was raised to 36° C. and samples taken at different time points were analyzed as described in Example 11. The maximum thymidine titer was 1.0 g/L after 18 hr, with a small amount of deoxyuridine.

Alternatively, strain CMG1158/pCG148 was grown as in Example 12, but in the medium composition presented in Table 10.

TABLE 10

| Medium composition (final concentration: g/L) | |
| --- | --- |
| K$_2$HPO$_4$ | 2 |
| K$_2$HPO$_4$ | 2 |
| (NH$_4$)$_2$HPO$_4$ | 3 |
| (NH$_4$)$_2$SO$_4$ | 2 |
| MgSO$_4$7H$_2$O | 0.4 |
| sorbitol | 100 |
| yeast extract | 30 |
| tryptone | 30 |
| proline | 2 |
| nicotinic acid | 0.1 |
| thiamine HCl | 0.1 |
| folic acid | 0.025 |
| p-aminobenzoate | 0.025 |

When the OD$_{600}$ reached 10, the culture was fed the following nutrients to give the indicated final concentrations (in g/L) uracil, 2; glycine, 1; methionine, 0.2; and serine, 1. The temperature was raised to 39° C., left there for 15 min, and then lowered to and maintained at 36° C., and time points were analyzed as described in Example 11. The maximum thymidine titer was 1.1 g/L after 18 hr.

Alternative or additional mutations and cloned genes are incorporated into strains of E. coli and B. subtilis expressing the dTMPase gene, and tested for production of thymidine, as described above. Selected strains produce a PdN such as thymidine, at concentrations in the medium of at least 10 g/L, at least 30 grams per liter, or at least 70 grams per liter, any of which is suitable for the commercial production of pharmaceutically-acceptable, antiviral compounds.

EXAMPLE 13

Production of a PdN (Deoxyuridine) in Shake Flasks at High Cell Density

Strain CMG1115 (see Table 4 above) can be modified to a genotype additionally including tdk+ (thymidine kinase) and thyA− (thymidylate synthase negative) in order to produce deoxyuridine in accordance with the present invention. Such a modified strain derived from strain CMG1115 (containing pCG144), is streaked on LB agar plates with 100 ug/mL ampicillin and 50 mg/ml thymidine and grown at 30° C. Single colonies are picked into 25 mL of LB broth with 100 μg/ml ampicillin in a 250 mL baffle flask and incubated at 30° C. for 8 hours. This culture (0.5 mL) is then used to seed flasks with production media with the composition presented in Table 11.

TABLE 11

| Deoxyuridine Production Medium | |
| --- | --- |
| K$_2$HPO$_4$ | 3.5 g/L |
| KH$_2$PO$_4$ | 1.5 g/L |
| (NH$_4$)$_2$SO$_4$ | 2.0 g/L |
| MgSO$_4$ | 0.4 g/L |
| sodium citrate | 0.5 g/L |
| calcium carbonate | 10 g/L |
| PP90BT (Deltown) | 8 g/L |
| glycerol | 50 g/L |
| thymidine | 0.2 g/L |
| biotin | 0.2 mg/L |
| thiamine | 1.0 mg/L |
| nicotinic acid | 1.0 mg/L |
| p-aminobenzoate | 1.0 mg/L |
| ampicillin | 0.1 g/L |
| ZnSO$_4$.7H$_2$O | 0.232 mg/L |
| MnSO$_4$ | 0.178 mg/L |
| H$_3$BO$_3$ | 0.056 mg/L |
| CuSO$_4$.5H$_2$O | 0.100 mg/L |
| Na$_2$MoO$_4$ | 0.039 mg/L |
| CoCl$_2$.7H$_2$O | 0.042 mg/L |
| KI | 0.066 mg/L |
| FeSO$_4$.7H$_2$O | 0.040 mg/L |
| NiCl.6H$_2$O | 0.0004 mg/L |
| phenol red | 0.1 g/L |

The 250 ml baffle flask containing 25 ml of production medium is incubated at 30° C. at 400 RPM in a NBS G25 shaker. When the culture has reached an optical density at 600 nm of 10 (read after dilution 1:11 into dilute sulfuric acid, 2 mL concentrated H$_2$SO$_4$ per 100 mL [to dissolve the CaCO$_3$ in the media]), at about 10 to 15 hours of incubation, the flask is shifted from the 30° C. shaker to a 37° C. shaker at the same RPM. At that time the media is also supplemented with 1.14 g/L D,L-methionine, 2.86 g/L glycine, 14.3 g/L autolyzed yeast (Ardamine YEP-S, Champlain Industries), uracil 2.8 g/L, and 0.25 mM IPTG. The pH in the flasks is maintained at approximately 7.0 through the addition of 4N NH$_4$OH as judged by the color of the phenol red indicator dye. Deoxyuridine concentration in the media would be expected to be at least 0.5 g/l.

EXAMPLE 14

Alternative Ten Liter Production of a PdN (Deoxyuridine) in a 14 Liter Fermentor To exemplify a ten liter production of PdN such as deoxyuridine, modified strain CMG1115 according to Example 13, above, is grown as above in a 14 Liter fermentor, but in the medium composition presented in Table 12.

TABLE 12

| Medium composition (final concentration: g/L) | |
|---|---|
| $K_2HPO_4$ | 7 |
| $NaH_2PO_4.H_2O$ | 3 |
| $NH_4Cl$ | 10 |
| $(NH_4)_2SO_4$ | 5 |
| $MgSO_4.7H_2O$ | 3 |
| glycerol | 125 |
| tryptone | 20 |
| thymidine | 0.2 |
| proline | 2 |
| nicotinic acid | 0.2 |
| thiamine HCl | 0.2 |
| folic acid | 0.025 |
| p-aminobenzoate | 0.025 |
| yeast extract | 10 |

When the $OD_{600}$ reaches 10, the culture is fed the following nutrients to give the indicated final concentrations (in g/L) for uracil, 3; glycine, 1; methionine, 0.2; and serine, 1. The temperature is raised to 36° C. and time points are analyzed as described in Example 11. The maximum deoxyuridine titer is about 1.0 g/L after 18 hr, with a small amount of thymidine.

Alternative or additional mutations and cloned genes are incorporated into strains of *E. coli, B. subtilis* or *Corynebacterium glutamicum*, expressing the dTMPase gene, and tested for production of deoxyuridine, as described above. Selected strains produce a PdN such as deoxyuridine, at concentrations in the medium of at least 10 g/L, at least 30 grams per liter or at least 70 grams per liter, any of which is suitable for the commercial production of pharmaceutically-acceptable, antiviral compounds.

What is claimed is:

1. A culture consisting essentially of a replicable microorganism comprising:
   a DNA sequence encoding a pyrimidine deoxyribonucleotide phosphohydrolase that converts a pyrimidine deoxyribonucleoside monophosphate to a pyrimidine deoxyribonucleoside, wherein said DNA sequence is expressed by said microorganism resulting in accumulation of said pyrimidine deoxyribonucleoside in culture medium containing said microorganism, and
   at least one mutation in a metabolic pathway that increases said accumulation of said pyrimidine deoxyribonucleoside in said medium.

2. A culture according to claim 1, wherein (A) said pyrimidine deoxyribonucleodide is thymidine, (B) said pyrimidine deoxyribonucleotide phosphohydrolase is thymidylate phosphohydrolase and (C) said pyrimidine deoxyribonucleoside monophosphate is thymidine monophosphate.

3. A culture according to claim 1, wherein (A) said pyrimidine deoxyribonucleoside is deoxyuridine, (B) said pyrimidine deoxyribonucleotide phosphohydrolase is thymidylate phosphohydrolase and (C) said pyrimidine deoxyribonucleoside monophosphate is deoxyuridine monophosphate.

4. A culture according to claim 1, wherein said chemical-resistance mutation comprises resistance to a compound selected from the group consisting of hydroxyurea, trimethoprim, an azidonucleoside, a cyanonucleoside, a halogenated nucleoside, and a halogenated nucleobase.

5. A culture according to claim 1, wherein said microorganism further comprises a heterologous DNA segment that encodes at least one metabolic enzyme or polypeptide such that the expression of said DNA segment further increases said accumulation of said pyrimidine deoxyribonucleoside in said medium.

6. A culture according to claim 5, wherein said metabolic enzyme is selected from the group consisting of carbamoyl phosphate synthase, aspartate transcarbamoylase, dihydroorotase, dihydroorote oxidase, orotate phosphoribosyltransferase, orotidine 5'-phosphate decarboxylase, CTP synthase, nucleoside-phosphate kinase, phosphoribosylpyrophosphate synthetase, nucleoside diphosphate kinase, ribonucleoside diphosphate reductase, dCTP deaminase, dUTPase, thymidylate synthase, serine hydroxymethyltransferase, dihydrofolate reductase, thioredoxin, thioredoxin reductase, dTTPase, dCTP pyrophosphatase, dCMP deaminase, uracil phosphoribosyltransferase, a thioredoxin reductase (trxB), a glutathione reductase, a glutathione synthase, a glutaredoxin, and a thymidylate synthase inhibitor polypeptide.

7. A culture according to claim 1, wherein said mutation is selected from the group consisting of a substrate analog-resistance mutation, a chemical-resistance mutation, a metabolic endproduct-resistance mutation, a purine-, pyrimidine-transport mutation, a nucleoside-transport mutation, and a metabolic enzyme activity mutation.

8. A culture according to claim 7, wherein said chemical-resistance mutation comprises resistance to a compound selected from the group consisting of hydroxyurea, trimethoprim, an azidonucleoside, a cyanonucleoside, a halogenated nucleoside, and a halogenated nucleobase.

9. A culture according to claim 7, wherein said mutation comprises resistance to a pyrimidine analog.

10. A culture according to claim 9, wherein said pyrimidine analog is selected from the group consisting of thiouracel, azauracil, fluorouracil, fluoroorotic acid, fluorocytidine, fluorodeoxyuridine, fluorodeoxycytidine, fluorouridine, azidothymidine, and pyrimidine dideoxyribonucleosides.

11. A culture according to claim 7, wherein said metabolic endproduct-resistance mutation comprises resistance to a purine analog.

12. A culture according to claim 7 wherein said metabolic endproduct-resistance mutation comprises resistance to thymidine.

13. A culture according to claim 7, wherein said substrate-analog resistance mutation comprises resistance to an amino-acid analog.

14. A culture according to claim 13, wherein said amino-acid analog is selected from the group consisting of a histidine analog, a tryptophan analog, an arginine analog, and a glutamine analog.

15. A culture according to claim 7, wherein said purine-, pyrimidine- or nucleoside-transport mutation comprises a nucleoside-transport mutation.

16. A culture according to claim 15, wherein said nucleoside-transport mutation is selected from the group consisting of a nupG nucleoside uptake mutation, a nupC nucleoside uptake mutation, and a tsx mutation for phage T6 resistance and nucleoside transport.

17. A culture according to claim 7, wherein said metabolic enzyme activity mutation comprises an inhibition of activity or amount of said enzyme.

18. A culture according to claim 17, wherein said enzyme comprises an enzyme selected from the group consisting of thymidine phosphorylase, uridine phosphorylase, thymidine kinase, and thymidylate synthase.

19. A culture according to claim 4, wherein said pyrimidine deoxyribonucleoside recovered in step (D) is obtained from medium with a pyrimidine deoxyribonucleoside concentration of at least about 1 g/L.

20. A culture according to claim 9, wherein said pyrimidine analog is selected from the group consisting of azidopyrimidine and a cyanopyrimidine.

* * * * *